(12) United States Patent
Johnston et al.

(10) Patent No.: US 7,791,009 B2
(45) Date of Patent: Sep. 7, 2010

(54) ELIMINATING ILLUMINATION CROSSTALK WHILE USING MULTIPLE IMAGING DEVICES WITH PLURAL SCANNING DEVICES, EACH COUPLED TO AN OPTICAL FIBER

(75) Inventors: Richard Johnston, Sammamish, WA (US); Eric Seibel, Seattle, WA (US); Charles David Melville, Issaquah, WA (US)

(73) Assignee: University of Washington, Seattle, WA (US)

( * ) Notice: Subject to any disclaimer, the term of this patent is extended or adjusted under 35 U.S.C. 154(b) by 427 days.

(21) Appl. No.: 11/945,901

(22) Filed: Nov. 27, 2007

(65) Prior Publication Data

US 2009/0135280 A1    May 28, 2009

(51) Int. Cl.
    *H01L 27/00* (2006.01)
(52) U.S. Cl. .................................. 250/208.1; 250/234
(58) Field of Classification Search ............ 250/208.1, 250/234–236, 216, 227.11, 227.2, 227.21, 250/227.26, 461.1; 600/407, 425, 473, 310; 348/262, 335, 281
    See application file for complete search history.

(56) References Cited

U.S. PATENT DOCUMENTS

| | | | |
|---|---|---|---|
| 4,695,163 A | 9/1987 | Schachar | 356/369 |
| 6,485,413 B1 | 11/2002 | Boppart et al. | 600/160 |
| 6,515,781 B2 | 2/2003 | Lewis et al. | 359/204 |
| 6,525,310 B2 | 2/2003 | Dunfield | 250/235 |
| 6,563,105 B2 | 5/2003 | Seibel et al. | 250/208.1 |
| 7,038,191 B2 * | 5/2006 | Kare et al. | 250/227.11 |
| 2001/0055462 A1 | 12/2001 | Seibel | 385/147 |
| 2003/0023141 A1 | 1/2003 | Stelzer et al. | 600/106 |
| 2005/0020926 A1 | 1/2005 | Wiklof et al. | 600/476 |
| 2005/0215854 A1 | 9/2005 | Ozaki et al. | 600/109 |

FOREIGN PATENT DOCUMENTS

EP    0 713 672    5/1996

(Continued)

OTHER PUBLICATIONS

Brown, M., and D.G. Lowe. "Recognising Panoramas" Proceedings of the Ninth IEEE International Conference on Computer Vision 0-7695-1950 Apr. 2003.

(Continued)

*Primary Examiner*—Que T Le
(74) *Attorney, Agent, or Firm*—Ronald M. Anderson

(57) ABSTRACT

A system includes a plurality of scanning devices and light receivers, enabling a plurality of images of a site to be displayed using output signals produced in response to light from the light receivers. To avoid crosstalk caused by light receivers receiving light emitted by a plurality of scanning devices, different wavebands of light can be applied to different scanning devices, the received light can be filtered, or the light can be supplied to one scanning device at a time to multiplex either frame-by-frame, or pixel-by-pixel, or the light supplied to each scanning device can be modulated and the received light demodulated so that an image is produced in response to light from a single scanning device. Expensive components such as laser light sources, optical detectors, a controller, and processor can be shared by multiple imaging devices to minimize the cost of the imaging system.

18 Claims, 16 Drawing Sheets

SERIAL SWITCHING – SAME WAVEBAND

FOREIGN PATENT DOCUMENTS

| | | |
|---|---|---|
| EP | 0 520 388 | 9/1996 |
| EP | 0 712 032 | 12/2001 |
| WO | WO 01/97902 | 12/2001 |

OTHER PUBLICATIONS

Kiesslich, Ralf, Martin Goetz, Juergen Burg, Manfred Stolte, Ekkhard Siegel, Markus J. Maeurer, Steven Thomas, Dennis Strand, Peter R. Galle, and Markus F. Neurath. "Diagnosing *Helicobacter pylori* In Vivo by Confocal Laser Endoscopy" Gastroenterology 2005;128 pp. 2119-2123.

Yelin, D., I. Rizvi, W.M. White, J.T. Motz, T. Hasan, B.E. Bouma, and G.J. Tearney. "Three-dimensional miniature endoscopy" *Nature* vol. 443, Oct. 19, 2006, p. 765.

Supplemental information for above article from *Nature*, Oct. 19, 2006. www.nature.com/nature/journal/v443/n7113/extref/443765a-s2.doc.

\* cited by examiner

SERIAL SWITCHING – SAME WAVEBAND

SPLITTING OPTICAL SIGNALS OF DIFFERENT WAVEBANDS

ELIMINATING ILLUMINATION CROSSTALK WHILE USING MULTIPLE IMAGING DEVICES WITH PLURAL SCANNING DEVICES, EACH COUPLED TO AN OPTICAL FIBER

BACKGROUND

In minimally-invasive therapeutic procedures, many of the tools that are used are designed to pass through a channel within a flexible endoscope, i.e., to fit within a lumen and be advanced to the distal end of the flexible endoscope. The endoscope is able to provide an image that the medical practitioner views while employing the tool to carry out the function for which it is designed. The general concept in designing the therapeutic tools that are currently used in such procedures is to make them compatible with available flexible endoscopes, which means that the tools must be substantially smaller in cross-sectional size than a flexible endoscope and must be configured to be usable when passed through the working channel contained within the flexible endoscope. This constraint on the size of the tools that can be used in minimally-invasive procedures tends to limit the types of tools that can be used and also makes the task of using such tools more difficult. It is likely that various types of diagnostic or therapeutic devices that might otherwise be used to treat a patient undergoing a minimally-invasive procedure would be of use in such procedures if not for the size limitation and other problems with use of the device while it is fitted through the working channel of an endoscope.

Accordingly, it would be desirable to develop a different approach that would enable various types of medical tools to be used in a minimally-invasive procedure, but without requiring that they be sufficiently small in size to pass through a conventional endoscope. Such tools are sometimes used to carry out a function at an internal site that is being separately imaged with an endoscope, but that approach typically requires another incision be made for the tool so that it can be passed transcutaneously into the patient's body and then advanced to the desired site where it will be employed. A catheter or conduit might be used for inserting a tool into an internal site, and it may be useful to provide an alternative approach for imaging the path followed by the catheter or conduit. A new approach should give greater emphasis to the use of a tool, a conduit, and/or a catheter within a patient's body, rather than to imaging at the site using a conventional endoscope. To achieve greater versatility in the use of tools, catheters, and conduits, it would be preferable to achieve a different approach to imaging an internal site either at the distal end of such devices or slightly proximal of the distal end. The imaging required to provide a visual field where the device is being used should be provided by means other than a conventional endoscope. It should be possible to image from behind the distal end of a device, as well as at its distal end. Furthermore, it should be possible to provide stereo images of a site where a tool or other device is being used internally without employing an endoscope. Stereoscopic images can be particularly useful because they provide more information about depth when using tools at a site.

It would therefore also be desirable to produce multiple images at disparate positions on one or more tools or components, since the multiple images can be employed to expand a limited field of view that is available from only a single image and position. Also, it would be desirable to use these images to view portions of a site that would otherwise be obstructed, if viewed from only a single position, as well as to view a site with the perspective provided by images created at disparate sites. A further desirable function would be to employ images made at different wavebands of light to extend the information about a site that is provided, relative to that provided by only a single such image.

To minimize costs and provide more efficient operation, it would also be desirable to enable a plurality of different imaging probes that are provided on tools and/or other devices so that they can share or multiplex share light source(s) and other components that are used to produce images of a site. Clearly, it would be more cost effective to share a base station that includes one or more light sources and image processing capability, with a plurality of imaging devices disposed on one or more tools or other components. In some cases, it may be desirable to share the same waveband of light produced by a single light source, which is shared by multiple imaging devices. Images might be produced by imaging devices either serially or in parallel. In other applications, it may be desirable to supply light from a plurality of different light sources and in different wavebands to a plurality of imaging probes disposed at the distal ends of tools or other components, for imaging an internal site.

The benefits of providing a system capable of imaging from multiple positions on one or more tools or components, and using the same base station is clearly not limited to medical applications. There are many other applications and environments for using imaging technology that can also benefit by providing imaging of a site from the distal end of one or more tools or components, such as a robot's end-effector, and from a plurality of locations on the one or more tools or components that share light source(s) and processing.

One concern that arises when plural imaging devices are used to image a site at the same time, for example, when producing a three-dimensional (3-D) image is that there can be substantial image noise due to illumination crosstalk. In this case, the two images used to produce the 3-D image are provided by two imaging devices that are spaced apart from each other a known distance, but scan almost the same area of the site. If scanning optical fibers are used to produce each of the images, they will scan an illumination spot over the surface at the site. The reflection from these spots is captured to produce each successive pixel of the respective images derived from the output signal of each scanning device. However, the reflection from the spot illuminated by one scanning optical fiber can be detected by the other imaging device, which can produce the crosstalk problem that causes poor image quality. Accordingly, it will be important to minimize crosstalk between different imaging devices that are scanning overlapping areas of a site.

SUMMARY

An exemplary system and method that produce a plurality of different images of a site with a plurality of imaging devices, while avoiding crosstalk in the images are disclosed below. The system includes a plurality of imaging devices that include a plurality of scanning devices and a plurality of light receivers. Each light receiver is associated with one of the plurality of scanning devices to receive light from an area of the site illuminated by one of the plurality of scanning devices. Further, each scanning device is coupled to a distal end of an optical fiber used to convey light to the scanning device so that the light is emitted by the scanning device to illuminate the site. The light receivers thus receive light from the site for use in producing images of the site. At least one light source is included for supplying light to the scanning devices through a plurality of optical fibers. Means are provided for imaging the site so as to prevent crosstalk between the plurality of images produced using the light received by the plurality of light receivers, by preventing light emitted by one of the plurality of scanning devices from interfering with light emitted by any other of the plurality of scanning devices.

The system further includes an optical switch that is controlled to direct light from the at least one light source, through an optical fiber, to a selected one of the plurality of scanning devices at a time. In at least one exemplary embodiment, the means for imaging so as to prevent crosstalk comprises a controller that is coupled to the optical switch. The controller controls the optical switch so that only one image of the site is permitted to be captured at a time by the plurality of imaging devices. In this manner, the images of the site are time multiplexed on a frame-by-frame basis. The plurality of scanning devices scan the site with light emitted in a desired scanning pattern, followed by a retrace interval to restart another scan. The controller causes the optical switch to selectively enable light to be supplied to a first scanning device scanning an area of the site while a second scanning device is in the retrace interval. The controller then causes the optical switch to selectively enable light to be supplied to the second scanning device scanning the area of the site while the first scanning device is in the retrace interval.

In a different exemplary embodiment, the means for imaging so as to prevent crosstalk comprises a controller that controls the optical switch so that light from the at least one light source is supplied to only one scanning device of a plurality of scanning devices that are scanning an area of the site at a time and only sufficiently long to scan a spot corresponding to a single pixel of an image of the site that is then being captured. Images of the site are thus pixel multiplexed so that the images are captured on a pixel-by-pixel basis, with only one pixel of each of the images being captured at a time.

The at least one light source can include a plurality of light sources, and one or more of the plurality of light sources are used only by one of the plurality of scanning devices. The one or more light sources used by one scanning device produce light at one or more wavebands that are different than the waveband of light produced by any other light source used by any other scanning device that illuminates a common portion of the site.

In a further alternative embodiment, the means for imaging so as to prevent crosstalk comprises a plurality of optical filters used to filter the light received by a plurality of light receivers that are receiving light from the common portion of the site illuminated by the plurality of the scanning devices. Specific optical filters of the plurality of optical filters pass light in one or more wavebands emitted by the scanning device associated with a specific light receiver that has received the light, but not light in a waveband emitted by a different scanning device. The plurality of optical filters can have different polarizations. In this case, the light emitted by each scanning device has a specific polarization matching that of the optical filter used to filter light received by the light receiver associated with the scanning device. Thus, only the light received from the site that was produced by the scanning device associated with a specific light receiver is used for producing an image of the site based on the signal output by the specific light receiver.

In yet another exemplary embodiment, the means for imaging so as to prevent crosstalk comprises a light modulator that modulates light provided to each scanning device differently, and a demodulator that demodulates output signals produced in response to the light received by the plurality of light receivers. The demodulator separates the output signals based on each different scanning device that produced the light that was reflected from the site and received by the plurality of light receivers, so that only light emitted by the scanning device with which a specific light receiver is associated is used to produce an image. The light modulator modulates light using either an amplitude modulation (AM) or a frequency modulation (FM) scheme.

The method includes steps that are generally consistent with the functions of the components of the system discussed above.

Another aspect of this technology is directed to an exemplary system and method for imaging a site. The system is shared by a plurality of scanning devices that emit light used to illuminate the site, and by a plurality of light receivers that receive light from the site. The system includes at least one display that can be employed for displaying images produced by imaging the site. A scanner controller controls the plurality of scanning devices and includes one or more light sources that produce light provided to the plurality of scanning devices for illuminating the site. The scanner controller also includes one or more detectors that detect light received from the site by the plurality of light receivers. Thus, the one or more light sources are shared between the plurality of scanning devices, and the one or more detectors are shared between the plurality of light receivers. A functional interface couples the plurality of scanning devices and the plurality of light receivers to the scanner controller. Also, a computing device is coupled to the at least one display, the scanner controller, and the functional interface and controls the system to produce the images of the site on the at least one display, without degradation due to interference between the light received by the plurality of light receivers that was emitted by the plurality of scanning devices.

In one exemplary embodiment, the scanner controller includes a different light source for each of two or more of the plurality of the scanning devices, so that light of different wavebands is emitted by the two or more of the plurality of scanning devices.

In another exemplary embodiment, the scanner controller operates in one of three modes. The three modes respectively include supplying light from the one or more light sources to only a single selected scanning device that is scanning an area of the site at a time; supplying light from the one or more light sources to the plurality of scanning devices at the same time, while ensuring that light emitted from only one scanning device of the plurality of scanning devices illuminates any area of the site at the time; and selectively supplying light from the one or more light sources to the plurality of scanning devices, using means to supply light with different characteristics to the plurality of scanning devices, so that each scanning device is supplied with light having a different characteristic than the light supplied to any other scanning device illuminating the same area of the site.

A corresponding method includes claims that are generally consistent with the functions performed by the components of the system just discussed.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter. Indeed it would be desirable to use non-standard means to provide enhanced and/or multiple views of a site where one or more tools or other components is to be employed.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

DESCRIPTION

Figure 1:
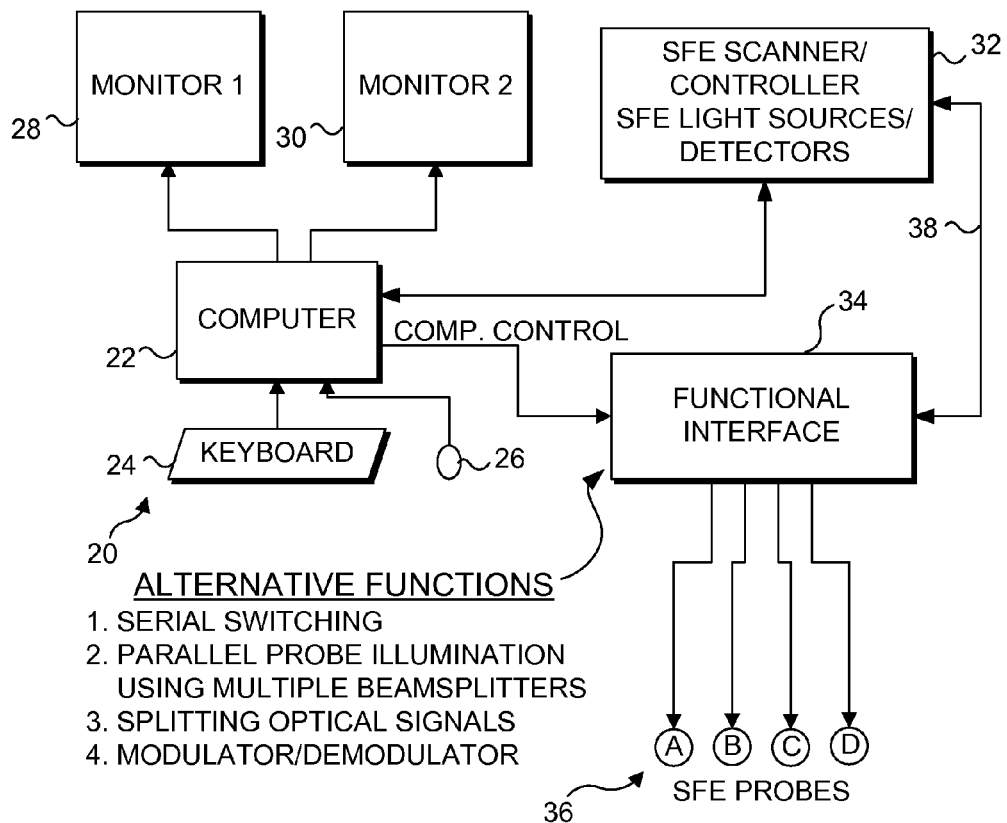
FIG. 1 is a functional block diagram illustrating components of an exemplary system having a single base station suitable for imaging using multiple probes, and including a functional interface that, depending upon the embodiment desired, can provide different alternative functions in connection with the probes.

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Overview of System for Imaging Using One Base Station for Multiple Probes

FIG. 1 illustrates an exemplary system that includes a single base station 20 that is used for imaging with multiple probes, which can be imaging devices disposed on one or more tools, or other components that are used at the site being imaged. Base station 20 includes a computer 22, which can be a general purpose personal computer or may be a more dedicated computing device specifically designed for the purpose of supporting the system for imaging with a plurality of probes. Computer 22 is coupled to a keyboard 24 that is used for input of text and control actions by a user, and to a pointing and/or input device 26, which can be mouse, trackball, foot pedal, or other type of device for controlling a position of a cursor and making selections on a graphic display, as input to computer 22. Also connected to computer 22 are a first monitor 28 and a second monitor 30, which can be used for displaying the images produced in response to output signals produced by a plurality of SFE probes 36 (labeled also as probes A, B, C, and D). It will be understood, that this system in not limited to only four such probes, but may include either more or fewer SFE probes, or may use other types of imaging devices.

Computer 22 is in bi-directional communication with an SFE scanner/controller and light sources/detectors box 32 via one or more optical fibers 38. Further details of the configuration of box 32 are discussed below. The SFE scanner/controller and light sources/detectors are also in communication with a functional interface 34 through which signals are conveyed to and from the plurality of SFE probes. Functional interface 34 is controlled by computer 22, which enables it to carry out one of at least four alternative functions, depending upon the particular configuration being used for the imaging system, as explained in detail below. These alternative functions include the use of the functional controller for serial switching of Red, Green, and Blue (RGB) laser light produced by the SFE light sources in box 32 between the plurality of SFE probes used in the system. The serial switching is carried out, for example, using a MEMS (or galvanometer controlled) mirror switch, as explained below in connection with FIG. 2. In the serial switching mode, all light received from the site being imaged using the plurality of SFE probes can be conveyed through collection optical fibers that extend from the distal ends of the SFE probes and are ganged together for group RGB light detection within box 32.

Figure 3:
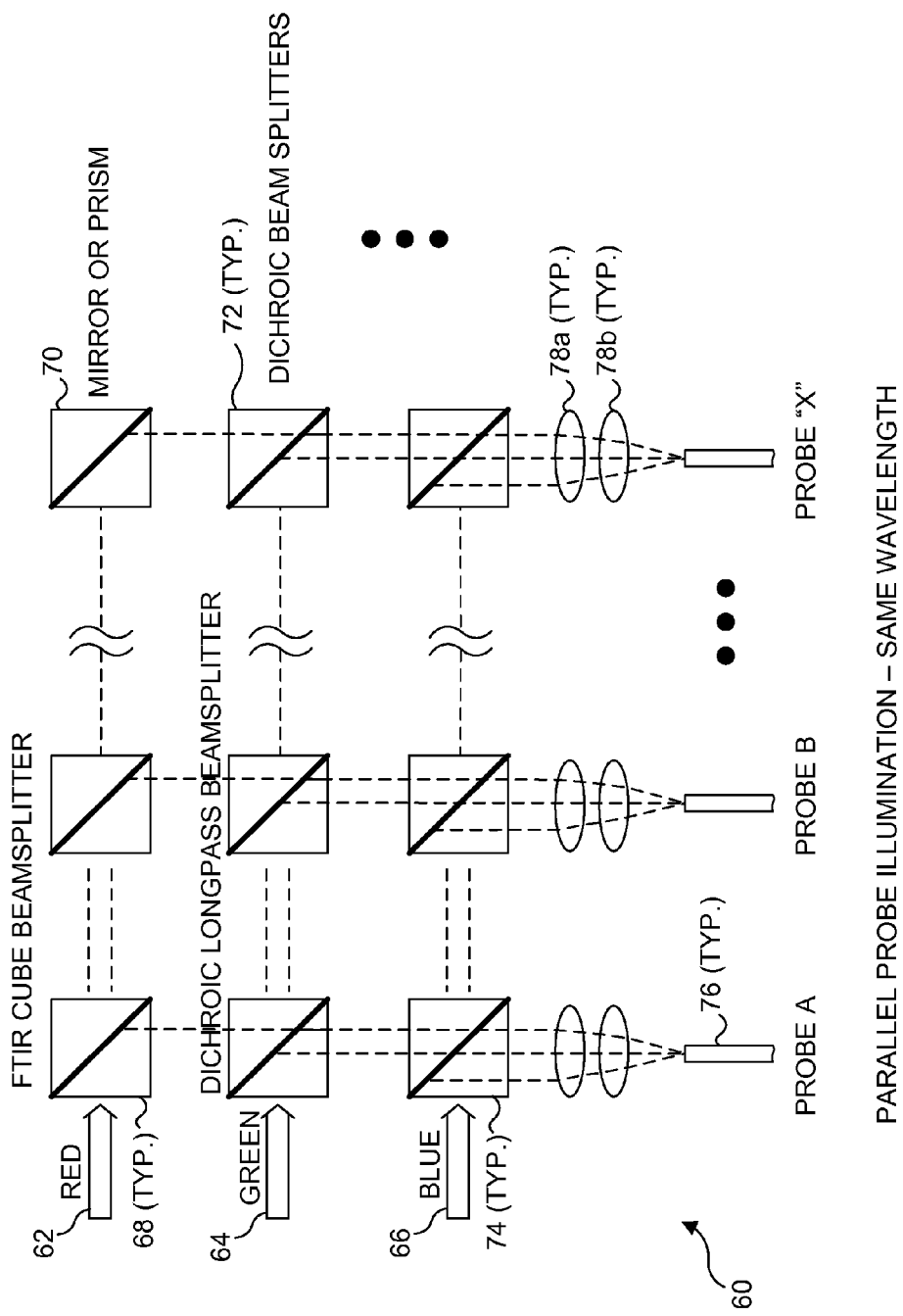
FIG. 3 is a schematic diagram of an exemplary configuration for providing parallel illumination to a plurality of probes using light of the same wavelengths from three different wavelength sources.

Functional interface 34 can alternatively be employed for carrying out the function of parallel probe illumination using multiple beamsplitters, as illustrated in detail in FIG. 3, which is discussed below. In this parallel probe illumination mode, the same wavebands of light are used for all SFE probes, and either frame sequential or pixel sequential time multiplexing will be applied in providing the light to each of the plurality of SFE probes. FIG. 3 illustrates an exemplary configuration showing how this mode can be implemented, as discussed in detail below.

A third alternative functionality provided by functional interface 34 is splitting optical signals. This mode of operation, separate RGB illumination fibers encompass different wavebands for multi-probe use. The light signals received from a site are then simultaneously split into separate wavebands before being detected. Further details are provided in connection with an example of this configuration shown in FIG. 4. As a further alternative (not shown in detail), the light supplied to one or more specific SFE probes can be polarized so that the polarization is in a specific orientation or mode. Light received from the SFE probes can then be filtered using an optical filter that passes only light having a polarization matching that of the light supplied to the one or more specific SFE probes, enabling the light received by different SFE probes to be separated before detection, based upon its polarization characteristics. In this way, only light supplied to the specific one or more SFE probes would be used for imaging a site.

Finally, the functions performed by functional interface 34 can include the modulation of the light supplied to each different scanning device from the one or more light sources, so that the light supplied to each different scanning device is modulated differently than the light supplied to any other scanning device. Further, the light received by one or more light receivers that are associated with a specific scanning device can be detected, producing output signals that are also demodulated with the matching demodulation, so that light modulated with a different demodulation will be filtered out. The modulation/demodulation that is applied by functional interface 34 can be either AM demodulation or FM demodulation, enabling the demodulation function to readily discriminate at a specified carrier frequency between the output signals produced by detecting the light from different light receivers, so that crosstalk between the different channels of imaging devices is avoided.

Figure 2:
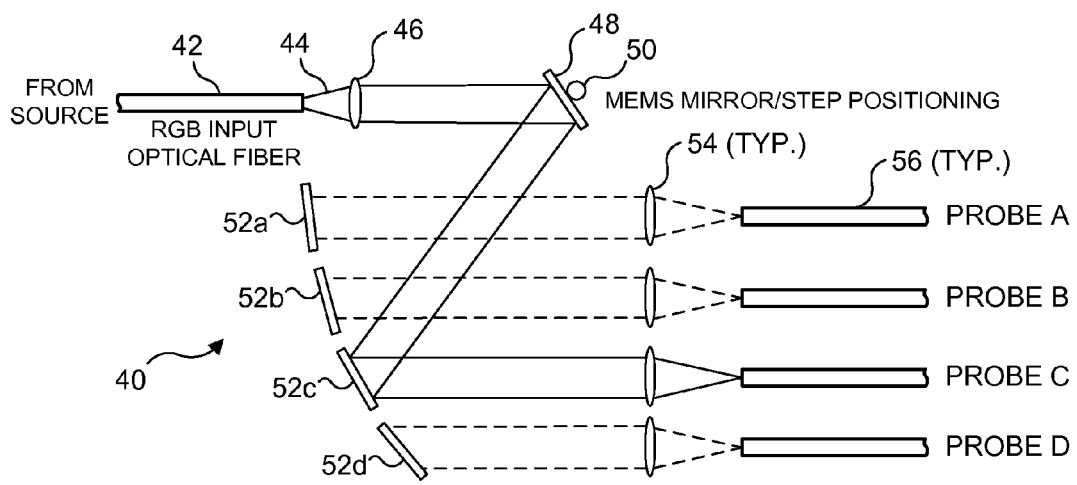
FIG. 2 is a schematic diagram of an exemplary approach for providing serial switching of light from a single source, so that the light is delivered sequentially to a plurality of different probes, for imaging purposes.

Referring now to FIG. 2, an exemplary serial switching configuration 40 is illustrated in which RGB light (or more generally, light of the same waveband) from a source (not shown) is conveyed through an input optical fiber 42 and is emitted along a path 44 directed toward a lens 46. Lens 46 focuses the light onto a MEMS mirror 48, which is coupled by a rotating shaft 50 to a rotational driver (not shown), so that the light is sequentially directed toward successive reflectors 52a, 52b, 52c, and 52d. The light is reflected by each of the reflectors in succession toward a lens 54, which focuses the light into one of optical fibers 56. In this example, there are four optical fibers 56, each of which conveys the light entering it from one of lenses 54 to one of probes A, B, C, or D. At the point in time shown in FIG. 2, the light is being reflected into the optical fiber that is coupled at its distal end to an SFE disposed on one of the tools or other components disposed at a site. Thus, only one of the probes is energized at a time, determined by controlling rotation of the MEMS mirror switch. It should be noted that it may be necessary to white balance each probe before it is used, to compensate for variations in coupling efficiency in serial switching configuration 40. Alternatively, a galvanometer-controlled mirror can be used in place of a MEMS mirror 48.

In FIG. 3, an exemplary configuration 60 illustrates how a plurality of probes 76 (identified as A-X) can be simultaneously supplied with light of the same wavelength. In this example, red light 62 from a source that is not shown enters from the left and is partially reflected by a frustrated total internal reflection (FTIR) cube beam splitter 68. The red light that is not reflected continues onto the left and is in turn also partially reflected. This process is repeated for each of the probes, until reaching a mirror or prism 70 for the last probe (i.e., for probe X), which reflects or redirects all of the remaining light downwardly toward a dichroic longpass beam splitter 72. Dichroic longpass beam splitter 72 is selected to transmit red light, but to reflect green light that has not been reflected by other dichroic longpass beam splitters that are in the path of green light 64 (entering from the left as shown in this Figure). Each preceding dichroic longpass beam splitter in this path reflects part of the green light downwardly, while transmitting red light that has been reflected downwardly from above. Thus, it will be apparent the dichroic longpass beam splitters 72 have the following characteristics: $\lambda_{cut} > \lambda_{green}$ and $\lambda_{cut} < \lambda_{red}$. Similarly, blue light 66 entering (from the left in this Figure) is partially reflected downwardly by each of a series of dichroic longpass beam splitters 74 that have been selected to partially reflect the blue light but to transmit red and green light that has been reflected downwardly from above. The combined RGB light is transmitted toward lenses 78a and 78b, which focus the RGB light into singlemode optical fibers coupled to the probes 76 (A-X). These probes thus simultaneously receive RGB light from the three sources. It will be understood that additional or fewer different wavebands of light may be similarly simultaneously provided to either more or fewer probes.

Figure 4:
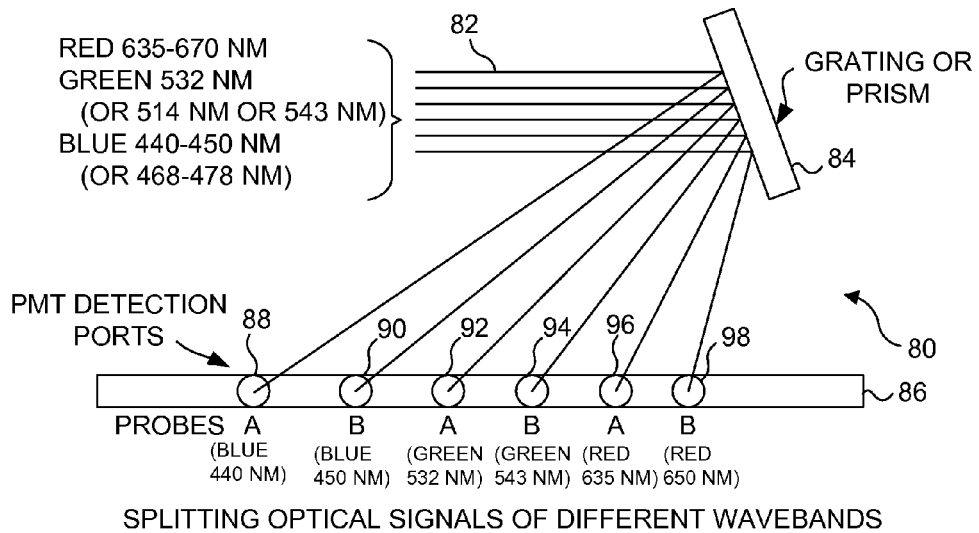
FIG. 4 is a schematic diagram illustrating an exemplary configuration for splitting optical signals of different wavelengths between a plurality of different probes used to image a site.

An exemplary configuration 80 for splitting optical signals of different wavebands is illustrated in FIG. 4. In this example, RGB light 82 that includes different wavebands is directed toward an optical grating or prism 84, which reflects each different waveband along a different path toward photomultiplier tube (PMT) detection ports 86. RGB light 82 includes red light covering the wavelength range 635 nm-670 nm (such as might be produced using laser diodes (not shown)), green light with wavelengths of 514 nm, 532 nm, and 543 nm (which can be produced using an Argon-ion laser, doubled 1064 nm laser, or He—Ne laser), and blue light with wavelengths of 440-450 nm, or 468-478 nm (produced, for example, by using Nichia™ blue laser diodes). Blue light with a wavelength of 440 nm is thus received at a PMT detection port 88, while blue light with a wavelength of 450 nm is received at a PMT detection port 90.

Similarly, green light at wavelengths of 532 nm and 543 nm are received respectively, at PMT detection ports 92 and 94, while red light at wavelengths of 635 nm and 650 nm are received respectively, at PMT detections ports 96 and 98. It will be apparent how this approach can be employed to use a single optical fiber (for example, an optical fiber having a distal end disposed to receive the light from a site) to convey multiple wavebands of light that are then split optically into different wavebands for input into different channels. The light that is thus split can also (or alternatively) include non-visible light, such as infrared or ultraviolet light. The optical frequency of light emitted from laser diodes can be tuned by varying the environmental conditions, such as temperature, of the laser diode. For example cooling the laser diode below room temperature can typically shift the optical frequency by over 10 nm, providing at least two laser wavelengths for each laser diode in operation.

Further Details of Exemplary System

Figure 5:
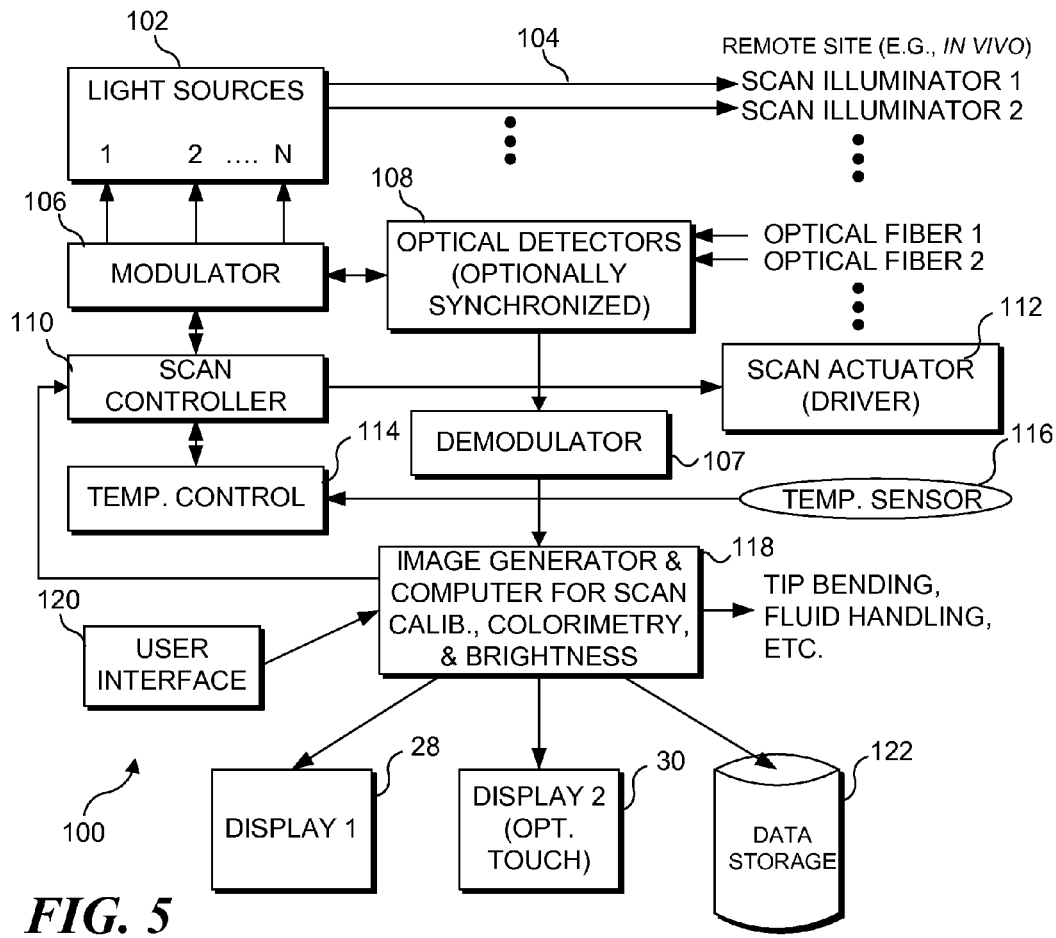
FIG. 5 is a more detailed functional block diagram of an exemplary system for imaging a site with scanning devices disposed at the distal ends of a plurality of tools, catheters, and/or conduits.

FIG. 5 illustrates an exemplary system 100 that is usable to provide imaging of a site at multiple locations disposed at the distal ends of one or more tools or other components. In this system, one or more light sources 102 (i.e., numbering from 1-N) provide light signals that are conveyed through one or more optical fibers 104 that have distal ends supported by the one or more tools or other components (not shown). The light provided to each scan illuminator by light sources 102 can be of the same waveband, or different wavebands, and can be controlled to be provided simultaneously, or serially to the scan illuminators. The one or more tools or other components are positioned at the site to be imaged, for example, where the tools or other components are to be used, so that light conveyed through optical fibers 104 can be used for a scanned illumination of the site. An initial application of this system would provide for imaging on medical tools or components that are disposed at an internal site within a patient's body; however, it is not intended that system 100 be limited to a medical application.

A modulator 106 is provided in the exemplary system of FIG. 5 and is used to modulate light sources 102, based upon signals supplied by a scan controller 110 in response to commands from a computer 118. The modulator acts as an optical switch to allow frame-to-pixel multiplexing by one or more scanning devices. Direct modulation of laser diode light sources is one exemplary method of multiplexing among different scanning devices. Laser diodes that can range in wavelength from ultraviolet, across the visible spectrum to infrared, can be directly modulated by switching their electrical power at rates above that of pixel sampling rates, e.g., greater than 20 million samples per second (>20 MHz). In the ultraviolet to blue spectral range, laser diodes at can be directly modulated at rates above 50 MHz, and suitable laser diodes are available from Nichia (Japan). Recently, green GaN-based laser diodes were announced by Rohm (Kyoto, Japan) as producing light with a wavelength of 532 nm, and with high modulation rates to match that of blue laser diodes. Alternatively, schemes for doubling the frequency of infrared laser diodes to achieve wavelengths of approximately 1064 nm have been prototyped by companies developing lasers for HDTV laser projection displays, which require the green light to be modulated at >50 MHz. These companies are Novalux (Sunnyvale, Calif.), Corning (Corning, N.Y.), and Osram Opto Semiconductors (Regensburg, Germany). Finally, red laser diodes which produce light at wavelengths of about 630-670 nm can be directly modulated at >50 MHz and are available from many manufacturers, such as Sony and Sanyo (Japan). The high modulation rates (>50 MHz) of the laser diode light sources enable optical switching or multiplexing at pixel rates.

Figure 12:
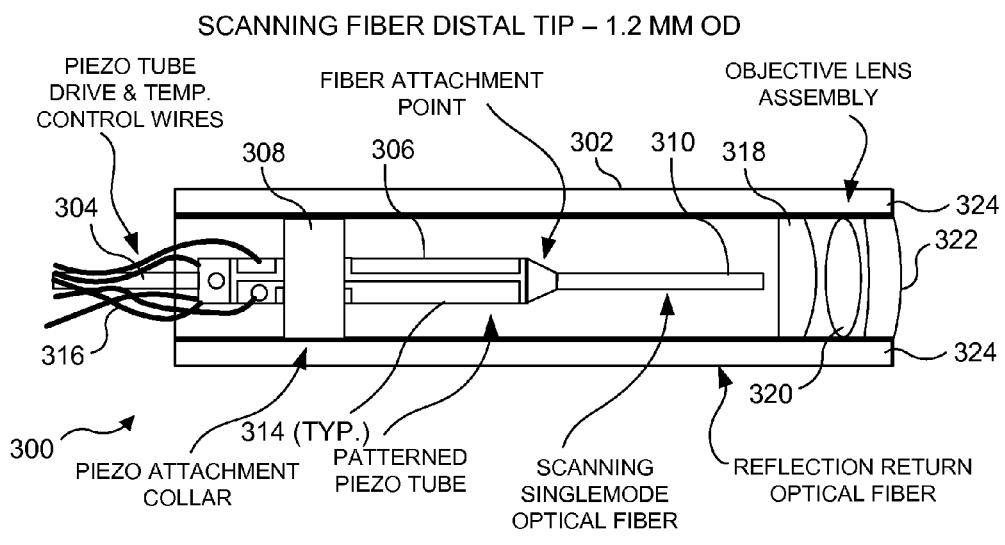
FIG. 12 is a cross-sectional view of an exemplary scanning fiber distal tip for use in imaging a site at a distal end of a tool, catheter, or conduit.

Current prototypes of a scanning fiber endoscope displaying 500-line red, green, and blue (RGB) images at 30 Hz require a pixel sampling rate of approximately 20 million samples per second. An exemplary forward viewing endoscope having a sub-millimeter scan illuminator and using a resonantly vibrating single optical fiber with a distal projection lens system and a ring of collection optical fibers surrounding the scanning fiber is illustrated in FIG. 12 and discussed in detail below. To provide pixel-rate multiplexing between two scanning fiber endoscopes using the same RGB laser wavelengths, pixels must be sampled between the two devices at twice the normal rate, i.e., at approximately 40 million samples per second. Higher pixel modulation rates may be required for a greater number of scanned imaging devices to eliminate crosstalk. Alternatively, the modulation rate of each light source can be significantly greater than the pixel sampling rates of a single imaging device. For example, a constant modulation rate of greater than 50 MHz can be used for the carrier frequency of the laser light sources, while the variation of the amplitude or AM (amplitude modulation) can occur as this beam of light is swept across the tissue. For spatially varying absorption and/or backscattering properties of the tissue being illuminated by this scanned laser light, the amplitude of this carrier wave can be employed to generate the image signal. As shown in FIG. 5, after detecting the optical signal using high-bandwidth optical detectors 108 (such as photomultiplier tubes), this AM signal can be demodulated at a modulator stage 106 (or at a separate demodulator stage 107). Thus, each imaging device can have its own carrier frequency specific channels or bands, which is analogous to the provision of different channels or stations in the radio transmission and reception arts. Since lasers emitting light in the ultraviolet to infrared wavelengths can be modulated at above the pixel rates, many cycles of laser illumination can be contained within one image pixel for AM signal detection without crosstalk from another probe imaging the same area.

In FIG. 5, computer 118 also is used for generating images based upon electrical signals that are received from optical detectors 108, and for scan calibration, colorimetry, and brightness control of light sources 102. In addition, computer 118 can produce control signals that are applied to bend the tip of a catheter, endoscope, or other tool that is being introduced to the site to be imaged, to facilitate introducing the device to the site around corners through a bifurcated lumen or other passage. Scan controller 110 also produces the scan actuator drive signals that are applied to each scan actuator (drive) 112 that is disposed at the distal end of the one or more tools or other components, to drive an optical fiber or mirror MEMS scanning device (not shown) to scan the site with light emitted in a desired predefined scanning pattern, such as a raster scan, helical scan, Lissajous pattern scan, etc.

A temperature control 114 is coupled to scan controller 110 and receives a temperature signal from each temperature sensor 116 disposed at the scanning illuminator, so that the scan controller can compensate for the temperature measured at the site, or adjust the temperature of the imaging device, as required. In some applications, a single temperature sensor 116 may be sufficient to monitor the temperature at the site, since temperature corrections can be applied to each scanning device used to image the site based upon the temperature thus sensed; however, in other applications, it is likely that each imaging device will have its temperature monitored and controlled independently, using a real-time control loop.

The light that was received from the site being scanned is conveyed through optical fibers and input to optical detectors 108, which can optionally be synchronized with the control of light sources 102, using a signal input from modulator 106. The intent in providing such synchronization is to ensure that the optical fibers only provide an input signal corresponding to the light directed to the site by a specific one of the different scan illuminators, which may be of a different waveband than the light provided by a different one of the scan illuminators. In this manner, the electrical output signals from the optical detectors corresponds only to the light received from the site when the site was illuminated by only the specific scan illuminator. The optical detectors can comprise PMTs, photodiodes, phototransistors, charge coupled arrays, or other light sensitive devices. While it is possible for the optical detectors to be disposed distally on the imaging device, size considerations and cost will likely provide a substantial benefit for the optical detectors to be disposed proximally and be shared between the imaging devices. In general, using a base station that includes more expensive components such as laser light source(s), processing capability, and optical detectors that are shared by a plurality of imaging devices will result in a more cost effective system. As explained herein, even though light sources are shared my multiple imaging probes that are imaging the same site, it is still possible to prevent crosstalk that causes interference in the light received from the site by an imaging device, even if that light is from a plurality of different scanning devices.

Under the control of a user interface 120, computer 118 can employ the electrical signals received from optical detectors 108 to produce displays of the images of the site on a display 1 monitor 28 (and/or on an optional display 2 touch screen or other monitor 30). Multiple images can be displayed on a single monitor, or the user can selectively switch between the images displayed on each monitor. Custom electronics or software techniques can be used to reconstruct an images from the output signals produced by detecting the light received by one or more imaging devices. Each imaging device can have a unique remapping file that is used to control image reconstruction, and reconstruction can be switched instantaneously between the imaging devices. The data used to produce these images and other relevant data collected during the imaging of the site can be stored for later retrieval, use, and processing in a data storage 122, which may comprise a local or remote hard drive or optical storage media, for example.

Figure 6:
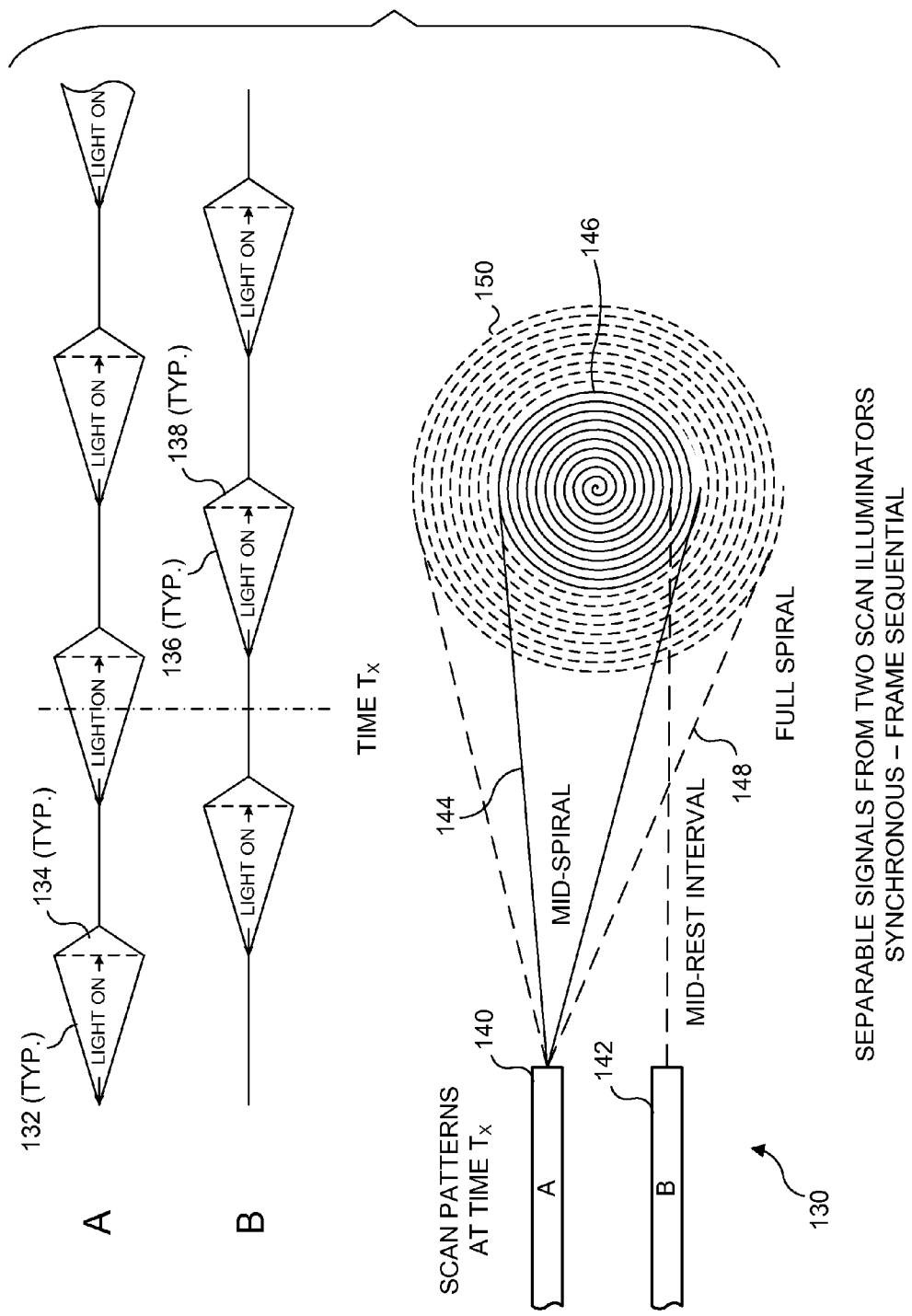
FIG. 6 is a schematic illustration showing how separable signals for two scan illuminators are used in a synchronous—frame sequential scheme for imaging a site.

It will generally be desirable for a plurality of scan illuminators to share the light source(s) and the other components system 100. Accordingly, to avoid problems that would occur if the site were illuminated by multiple scan illuminators at the same time, it will be desirable to multiplex or use other techniques that separate the signals for each different probe or scan illuminator in time. FIG. 6 illustrates a timing diagram and configuration 130 showing how different scan illuminators 140 and 142 can be energized to illuminate a site at different times, so that the light received from the site that is detected and used to produce images is synchronized with the source of the illumination of the site and not a mix of reflected light from the site for two different illumination light sources. Accordingly, scan illuminator A in FIG. 6 is controlled so that the illuminator produces a scanning light beam during successive time intervals 132 and then returns to a rest state during a time interval 134. When interval 134 starts, scan illuminator B, which has been off and in a rest state, begins scanning for a time interval 136, and thereafter returns to its rest state during a time interval 138. Thus, only one of the scan illuminators is actively scanning a site at a time. The lower portion of FIG. 6 illustrates scanning light 144 being emitted from a distal end 140 of scan illuminator A at a time $T_x$, which is at a mid-spiral point 146 in a full helical scanning spiral scan 150 that scanning light 148 will produce at the end of time interval 132. Scan illuminator B is at about a mid-point in its rest interval at time $T_x$ and is thus not providing any illumination of the site at that point in time.

Figure 7:
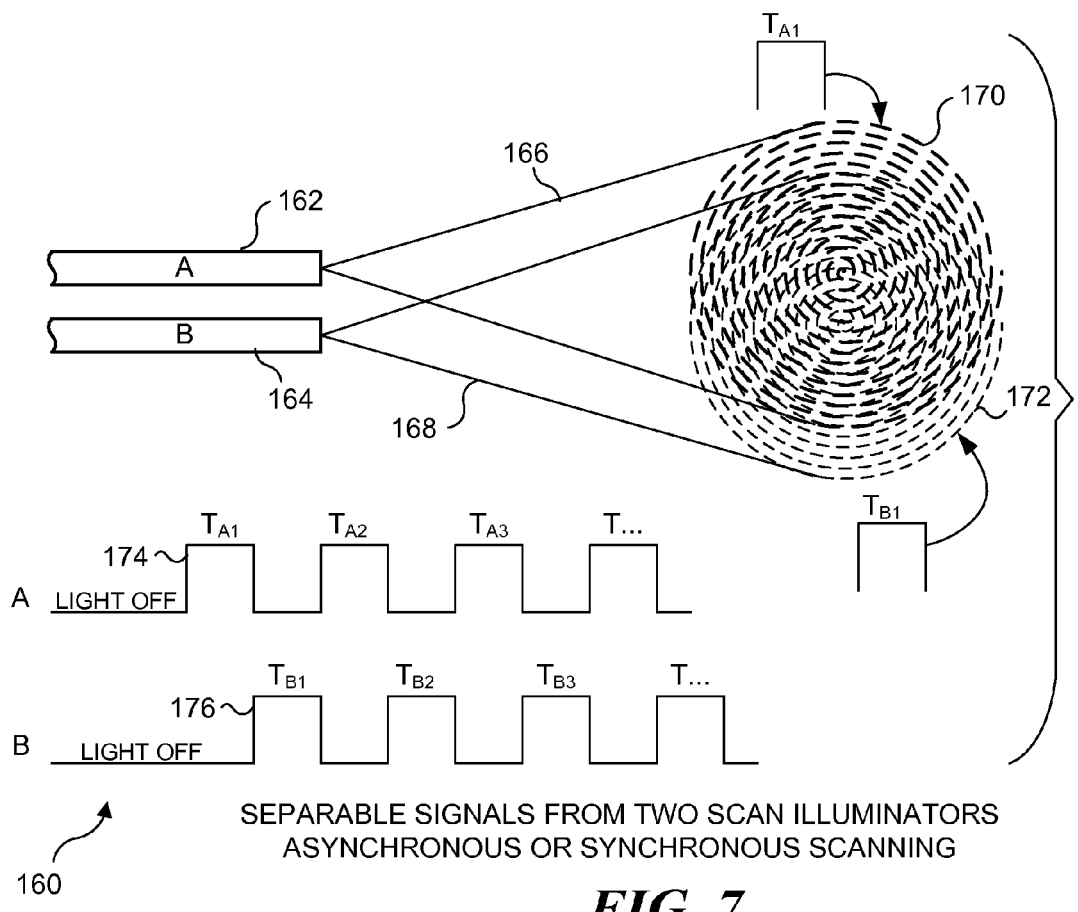
FIG. 7 is a schematic illustration showing how separable signals for two scan illuminators are used in an asynchronous or synchronous scheme for imaging a site.

An alternative approach for controlling scan illuminators A and B so that they produce separable light signals 166 and 168 (which can be asynchronous or synchronous) is illustrated in an exemplary configuration 160 in FIG. 7. In this approach, a helical scanner 162 is provided with pulses 174 of light while producing a spiral scan 170 of a site. Similarly, a helical scanner 164 is provided with pulses 176 of light while producing a spiral scan 172. The signal that energizes the light sources used for producing the respective spiral scans by these two scan illuminators can be synchronized with the detection of light from the site and can be pixel sequential. This approach reduces any potential photo-toxicity by spreading out tissue light exposure over time. The pulse sequence for the light pulses used for each of the scan illuminators is shown in the lower portion of the Figure.

Advantages of Imaging a Site from Multiple Positions

Figure 8A:
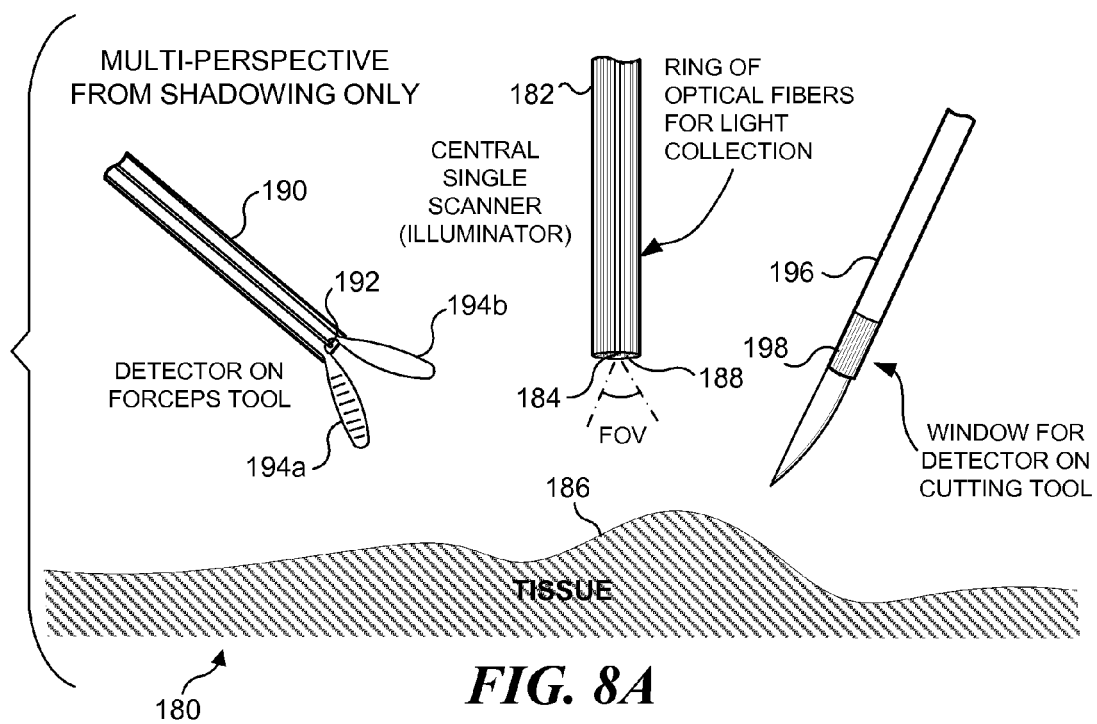
FIG. 8A is a schematic diagram illustrating how an internal site can be imaged in a multi-perspective view using detectors disposed on the distal ends of a plurality of spaced-apart instruments or tools.
Figure 8B:
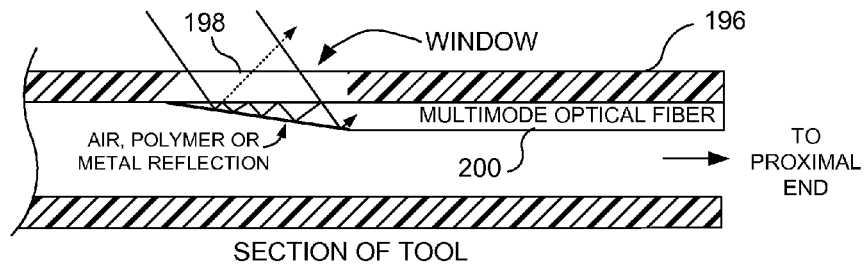
FIG. 8B is a cross-sectional view of a distal portion of an exemplary tool showing how light entering a side window is conveyed through a multimode optical fiber to a proximal end of the tool.

FIG. 8A illustrates an example 180 showing the use of the present novel approach in laparoscopic surgery, wherein a multi-perspective view provided by imaging from a plurality of spaced-apart locations on the distal ends of a plurality of medical tools is useful in more effectively viewing the site on which the medical tools are being used. The resulting shadowing of tissue 180 provided in the images of the site that is illuminated in this example by a single central scanner illuminator 184 included in the distal end of an endoscope 182 improves the perspective view of the tissue, so that details of the site are more evident. The field of view (FOV) of the central scanner illuminator illuminates tissue 186 with light in a desired scanning pattern. Light reflected from the tissue is received by a plurality of optical fibers 188 arrayed in a ring around the central scanner illuminator and is conveyed proximally to detectors (not shown in this Figure), for use in producing an image of the site. A forceps tool 190 includes a return optical fiber 192 in its central core that also receives light from tissue 186 illuminated by the central scanner illuminator in the endoscope. The light reflected from the site enters the distal end of this return optical fiber in the forceps tool, between the open ends of forceps grippers 194*a* and 194*b*. A third position for imaging the site is disposed on a cutting tool 196, which includes windows 198 that receive light reflected from tissue 186, but at a different angle than either return optical fiber 192 and the ring of optical fibers in the endoscope. The light passing through windows 198 in the cutting tool is conveyed proximally through multimode optical fibers 200 (only one shown), as illustrated in the cross-sectional view of a portion of cutting tool 196 in FIG. 8B. The light enters windows 198 from the side of the cutting tool and is internally reflected multiple times at the interface between the cleaved distal end of multimode optical fiber 200 and the air, polymer, or metal interface in the cutting tool.

Figure 9A:
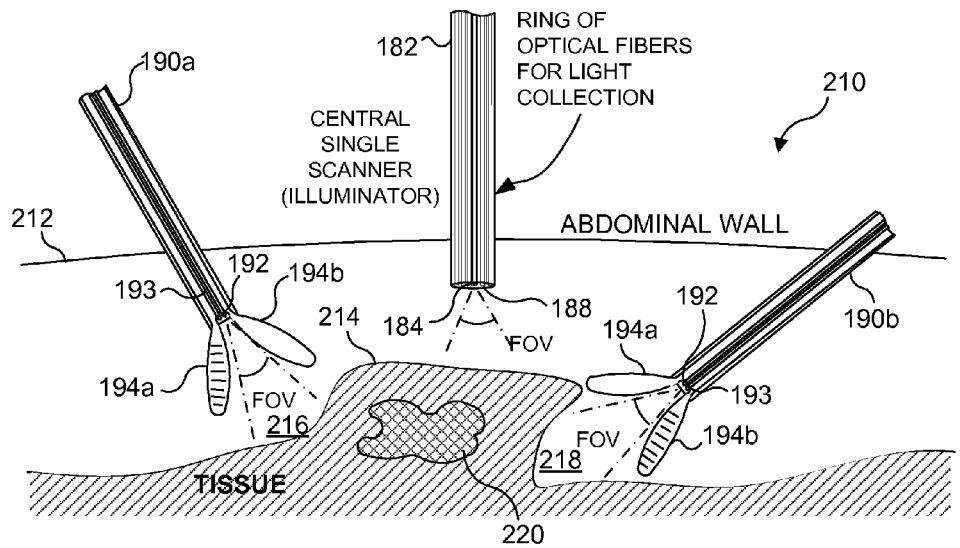
FIG. 9A is a schematic diagram illustrating how an internal site that includes otherwise obscured areas can be imaged using detectors disposed on the distal ends of a plurality of spaced-apart instruments or tools.

An advantage of imaging a site with a plurality of scan illuminators and detecting the light from a plurality of disparate locations on the distal ends of tools or components is illustrated in an example 210 shown in FIG. 9A. In this example, endoscope 182 extends through an abdominal wall 212. Central scan illuminator 184 in the endoscope scans a portion 214 of tissue adjacent to the distal end of the endoscope with light in a desired scan pattern, and the ring of optical fibers 188 receive and convey light reflected from portion 214 of the tissue. The tissue at the internal site forms a ridge or hump, so that another portion 216 of the tissue is outside the FOV of the scan illuminator of endoscope 182, and another portion 218 of the tissue is hidden by the overhanging shape of the tissue ridge or hump, which is in a deep shadow relative to the FOV illumination of the central scan illuminator of endoscope 182. However, in this example, two forceps tools 190*a* and 190*b* also extend through the abdominal wall, on opposite sides of endoscope 182. Each of these forceps tools include a central scan illuminator 193 that illuminates the tissue, but from different directions and from positions that are on each side of the central scan illuminator in endoscope 182. Accordingly, light reflected from portion 216 of the tissue is received at the distal end of return optical fiber 192 in left forceps tool 190*a*, while light reflected from portion 218 of the tissue is received by return optical fiber 192 in forceps tool 190*b* on right side of the endoscope. Effectively, the use of a plurality of scan illuminators at disparate positions that provide scan illumination of a site from different angles greatly improves the visibility of the site in the images produced by the system and thus effectively extends the FOV of the imaging provided by only a single scan illuminator that detects light only at the distal end of one tool or component.

Within the tissue 214 of FIG. 9A is an object of interest, such as a tumor 220, which is expected to interfere with the light from right forceps tool 190*b* illuminating a portion 218 of the tissue. For example, this light interference may result from an increased light absorption compared to the light absorption of surrounding tissue that can be detected by right forceps tool 190*b* or by another tool with imaging capability.

In this example, the increased absorption contrast may be detected from the backscattered optical signal to right forceps tool 190*b* illuminating portion 218 of the tissue. Alternatively, the increased absorption contrast may be detected from the side scattered optical signal to endoscope 182, or be detected from the transmitted optical signal to left forceps tool 190*a* through portion 216 of the tissue. In this example, the tools with imaging capability are sharing optical signals, to provide the user with enhanced shadowing from different perspectives and enabling both imaging in reflection and transmission within the same region of the body. In these limited cases where the illumination fields of view do not overlap directly, it may not be necessary to employ any method for reducing crosstalk.

Figure 9B:
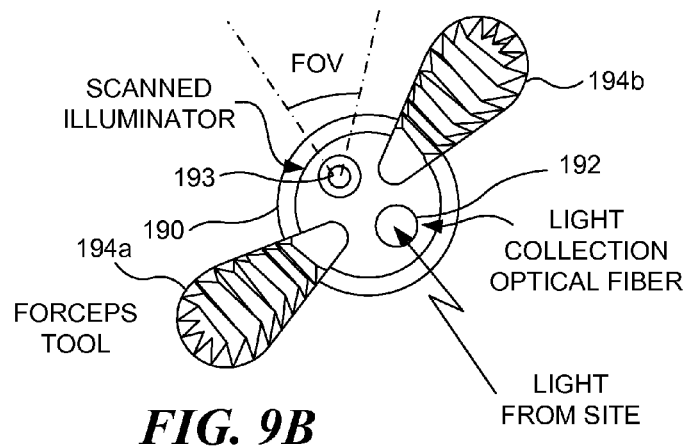
FIG. 9B is a schematic diagram of a distal end of an exemplary forceps tool, illustrating the disposition of a scanned illuminator and a light collection optical fiber.

Details of the distal end of forceps tool 190 are illustrated in FIG. 9B. As shown therein, the distal ends of scan illuminator 193 and of return optical fiber 192 that receives and collects light from a site are disposed between grippers 194*a* and 194*b*. Thus, the forceps tool can image a site on which the forceps tool is being used to grip tissue or other material.

Figure 10:
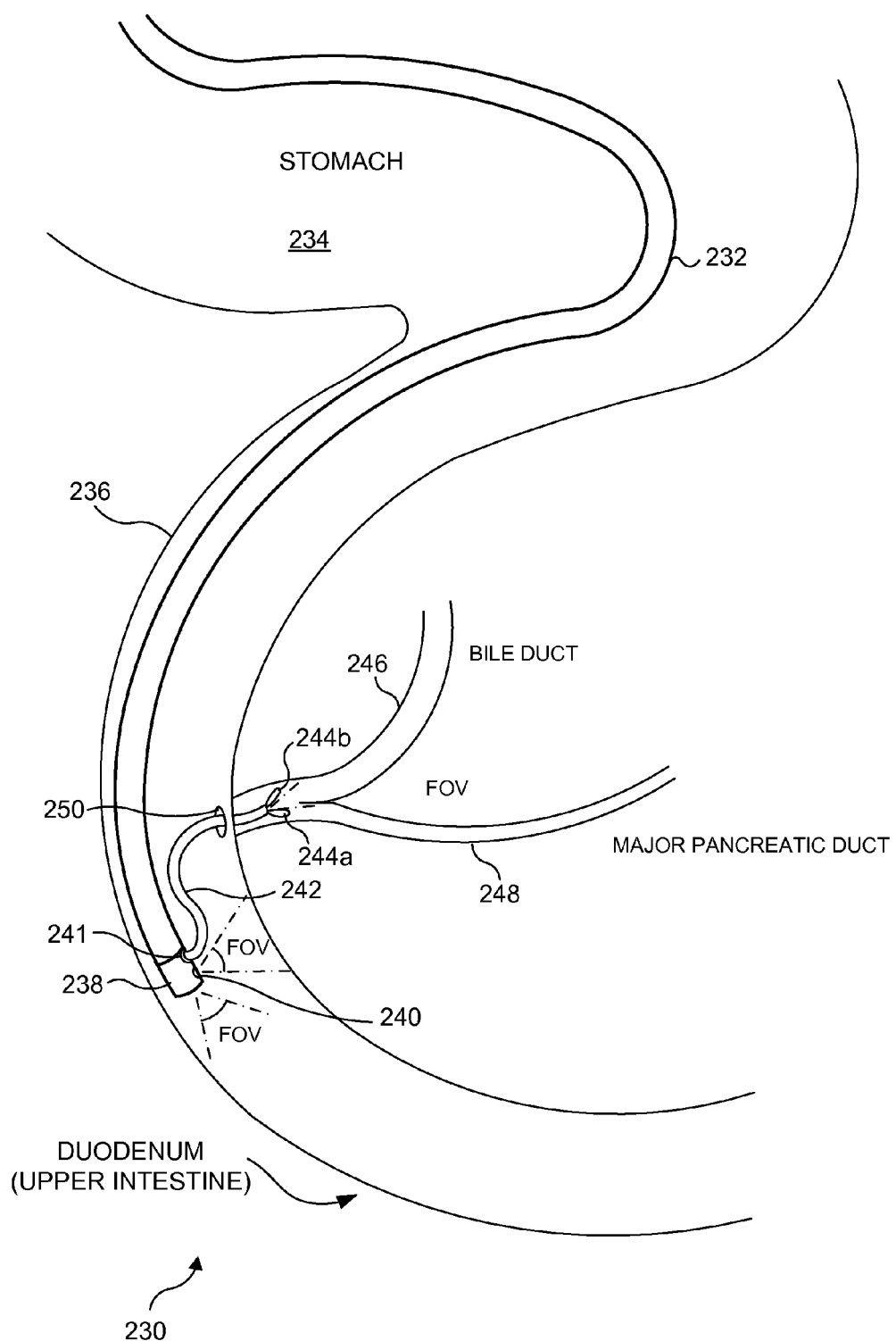
FIG. 10 is a schematic view of a portion of a stomach and duodenum, showing how an exemplary mothertool is used for imaging forward, while a childtool with distal imaging capability is advanced through a side port of the mothertool and advanced through a lumen leading to the bile duct and major pancreatic duct.

Another medical example 230 is provided in FIG. 10, which schematically illustrates a motherscope 232 designed for being passed down an esophagus into a stomach 234 and passing then into a duodenum 236 of a patient. Motherscope 232 includes a forward viewing scan illuminator and corresponding optical fibers for receiving light illuminated in the forward FOV ahead of a distal end 238 of the motherscope. A side-viewing scan illuminator 240 is also provided at the distal end of the motherscope to scan toward the side, generally orthogonal to the longitudinal axis of the motherscope. Not visible in this Figure is a return optical fiber that receives light reflected from tissue at the side of the distal end of the motherscope that was illuminated by the side-viewing scan illuminator. The motherscope uses its imaging capability to assist an operator in advancing the distal end of the motherscope into the duodenum and for locating an opening 250 from the duodenum into a bile duct 246 and one main pancreatic duct 248.

Adjacent to side-viewing scan illuminator 240 is disposed a side port 241 through which extends a daughterscope 242 comprising a forceps tool that includes grippers 244*a* and 244*b*. Disposed on the distal end of daughterscope 242, between the two grippers (but not visible in this Figure) is a forward-viewing scan illuminator, generally configured as shown for forceps tool 190 in FIG. 9B. The FOV of this forward-viewing scan illuminator can be employed to assist the operator in advancing the forceps tool at the distal end of the daughterscope into either of the bile duct or the major pancreatic duct, to take a tissue sample, or for some other purpose. The multiple imaging capability of the motherscope and daughterscope thereby greatly facilitate completing tasks of this nature by providing more complete imaging capability than might be accomplished with only a single image device.

Figure 11A:
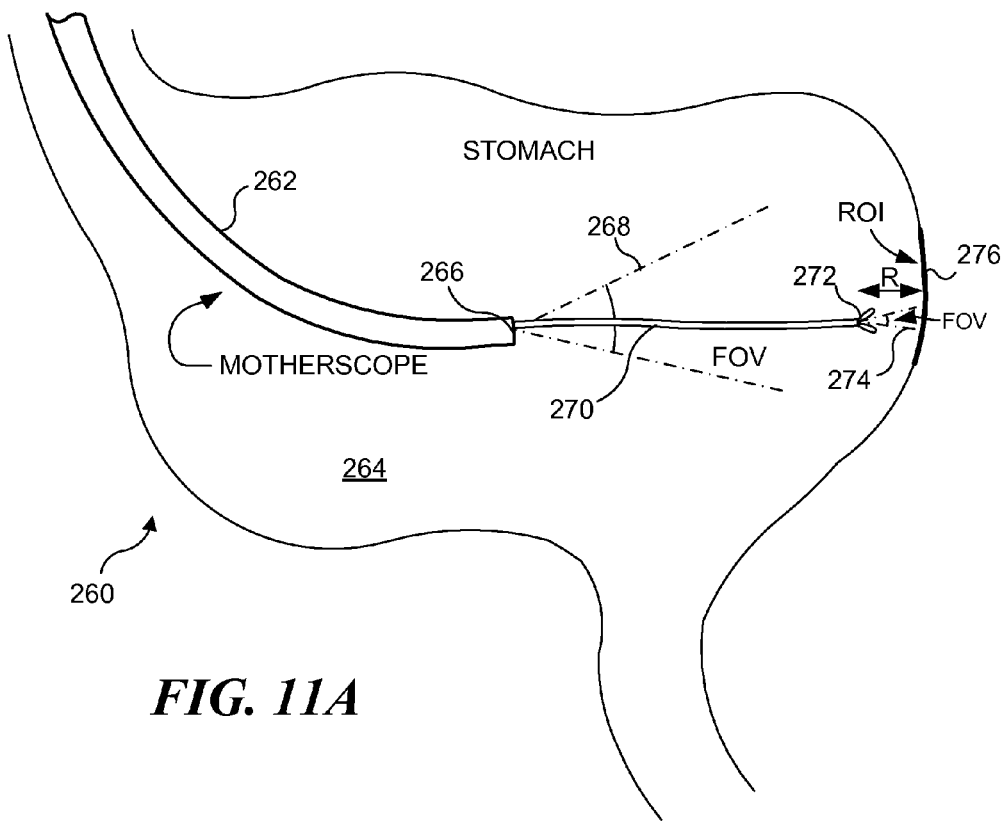
FIG. 11A is a schematic view of a stomach, showing how a motherscope with forward imaging and a childtool with imaging capability are used to image a region of interest (ROI) along a wall of the stomach.

FIG. 11A illustrates an example 260 of a motherscope 262 having a forward-viewing scan illuminator 266 with a FOV 268 at its distal end, and a return optical fiber for receiving light from tissue and other objects within the FOV of the forward-viewing scan illuminator. Motherscope 262 has been advanced into stomach 264 of a patient in this example. A daughterscope 270 having forceps tool 272 at its distal end is also provided with a forward-viewing scan illuminator having a FOV 274 directed toward a region of interest (ROI) 276. The forceps tool can thus readily image the ROI and selectively take a tissue sample where desired. The forward-viewing scan illuminator on motherscope 262 and the forward-viewing scan illuminator on daughterscope 270 image the wall of the stomach at different distance from the ROI. The forward-viewing scan illuminator on daughterscope 270 can have more highly focused light at the more closely located ROI 276 compared to motherscope 262, enabling a return optical fiber (not visible in this Figure) to receive reflected light to produce an image with greater spatial resolution than that produced in response to the light received from the return optical fiber in the motherscope, but with less depth of focus (DOF). Accordingly, providing these two scan illuminators with different characteristics of FOV and DOF can enhance the capability of the overall system to perform certain tasks. Alternatively, daughterscope 270 can illuminate with light that causes fluorescence signals to be emitted from a site, and such signals are typically much weaker than backscattered laser illumination. Fluorescence signals can be used to form diagnostic images of the ROI, to gather information on the health of the tissue using a different mode of optical interrogation of the tissue. Simply positioning daughterscope 270 closer to ROI 276 than motherscope 262 will significantly increase the collection efficiency of the optical signal, since intension decays by $(1/R)^2$, where R is the separation distance between distal tip of the daughterscope and the ROI. In addition, daughterscope 270 may provide stereo, depth-enhanced viewing of the ROI or deeper tissue imaging using light at infrared optical frequencies and optional biomarker enhancement of tissue specific image contrast mechanisms.

Figure 11B:
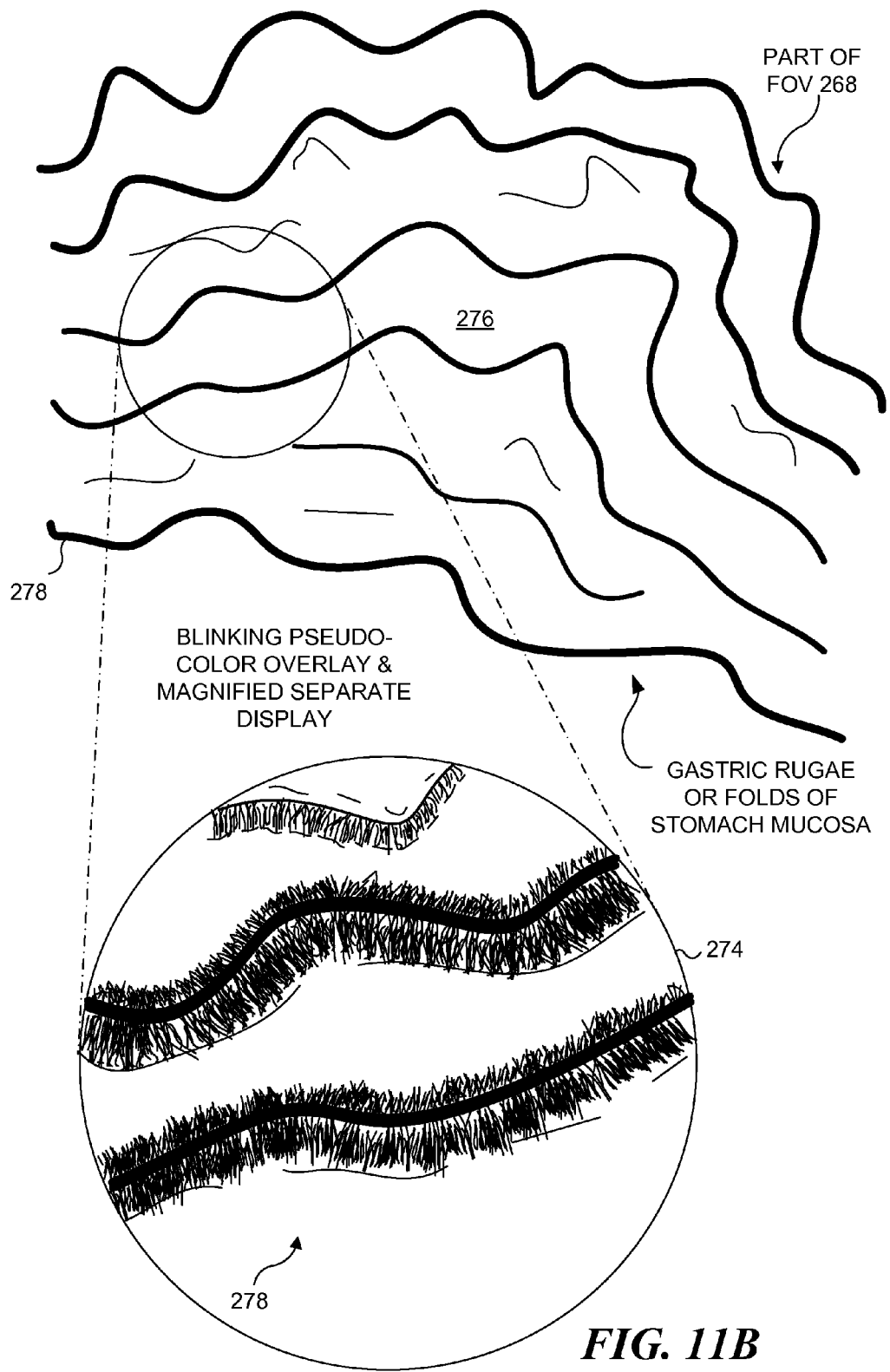
FIG. 11B is a schematic view of exemplary images of a ROI along the wall of the stomach, as displayed to the user of the motherscope and childtool of FIG. 11A.

FIG. 11B illustrates the images of ROI 276 that are displayed to the user using the signals from motherscope 262 and daughterscope 270. In motherscope image 274, gastric rugae or folds 278 of the mucosa lining the stomach are displayed at low resolution with simple color imaging of the backscattered light. Within this image of the ROI is an insert image provided by the extended daughterscope at a much closer separation distance R, yielding a magnified view of gastric folds 278. Furthermore, the contrast is enhanced by a topically applied fluorescence dye (e.g., acriflavine hydrochloride) that provides high-contrast fluorescence labeling of Helicobacter pylori or other bio-specific cells of interest that are not visible in the motherscope image. Once the daughterscope is advanced from the motherscope, the motherscope image no longer has an unobstructed view of ROI 276. The daughterscope view could be minimized and stitched into the obstructed part of the motherscope view using techniques described below.

Exemplary Scan Illuminator and Return Optical Fibers

While other designs for scan illuminators can be employed, an example of a scanning fiber illuminator and imager 300 is illustrated in FIG. 12. Scanning fiber illuminator and imager 300 includes a flexible single mode optical fiber 304 that passes through a patterned tube of piezoelectric material 306, which serves to drive a distal end 310 of the optical fiber to move in a desired scanning pattern. Distal end 310 extends distally beyond the patterned tube of piezoelectric material and is cantilevered from it, adjacent to a distal end of the tool or other component on which the scanning fiber illuminator is mounted or supported. The patterned tube of piezoelectric material is held in place by a piezo attachment collar 308. Quadrant electrodes 314 are plated onto the patterned tube of piezoelectric material and can be selectively energized with an applied voltage in order to generate two axes of motion in distal end 310 of optical fiber 304. Lead wires 316 carry electrical voltage signals to each of the quadrant electrodes to energize the piezoelectric material relative to each axis of motion and also convey temperature control signal to a temperature control (not shown). In this exemplary embodiment, the two axes in which the distal end of the optical fiber are driven are generally orthogonal to each other. An amplified sine wave applied to one axis and a cosine wave applied to the other axis of the patterned tube of piezoelectric material can generate a circular scan, although those of ordinary skill in the art will understand that a variety of different scan patterns can be produced by appropriately moving distal end 310 of optical fiber 304. An appropriate modulation of the amplitudes of the electrical voltage signals applied to the quadrant electrodes can create a desired area-filling two dimensional pattern for imaging with light emitted from distal end 310 of the optical fiber. A few examples of the various scan patterns that can be achieved include a linear scan, a raster scan, a sinusoidal scan, a toroidal scan, a spiral scan, and a propeller scan. In some exemplary embodiments, the distal end of the optical fiber is driven so that it moves at about its resonant (or near-resonant) frequency, which enables a greater scan amplitude to be achieved for the given drive signals applied.

Other types of scanning mechanisms that can alternatively be used for imaging at the distal end of a tool or other component include a MEMS scanner (not shown) that has a scanning beam used to optically scan an internal site with light to produce an image of the internal site that might instead be used. An example of a MEMS scanner for imaging is shown in commonly assigned U.S. Pat. No. 6,975,898, the disclosure and specification of which are specifically hereby incorporated herein by reference. A reflective mirror can also be driven to scan a site with light conveyed to the distal end of a tool or other component, as will be known to those of ordinary skill.

Light emitted from distal end 310 as it moves in the desired scan pattern travels through lenses 318, 320, and 322 and is directed at a site forward of the scanning fiber illuminator. The overall diameter of the scanning fiber illuminator is typically 1.0 mm or less. Light reflected or scattered by the site illuminated with the scanning light is then detected and used to provide the imaging function. In this exemplary embodiment, an annular ring 302 of return optical fibers is disposed around the distal end of the scanning fiber illuminator and has a typical outer diameter that is less than 2.0 mm. Light from the site passes into distal ends 324 of the return optical fibers and is conveyed proximally to detectors in a base station, as discussed above. The output signals produced by the detectors are then used to produce an image of the site that is proximate to the distal end of the scanning fiber illuminator. As mentioned above, a side-viewing illuminator can employ a reflective surface or mirror (not shown) and can then readily image a site at one or more sides of the scanning fiber illuminator.

Figure 13:
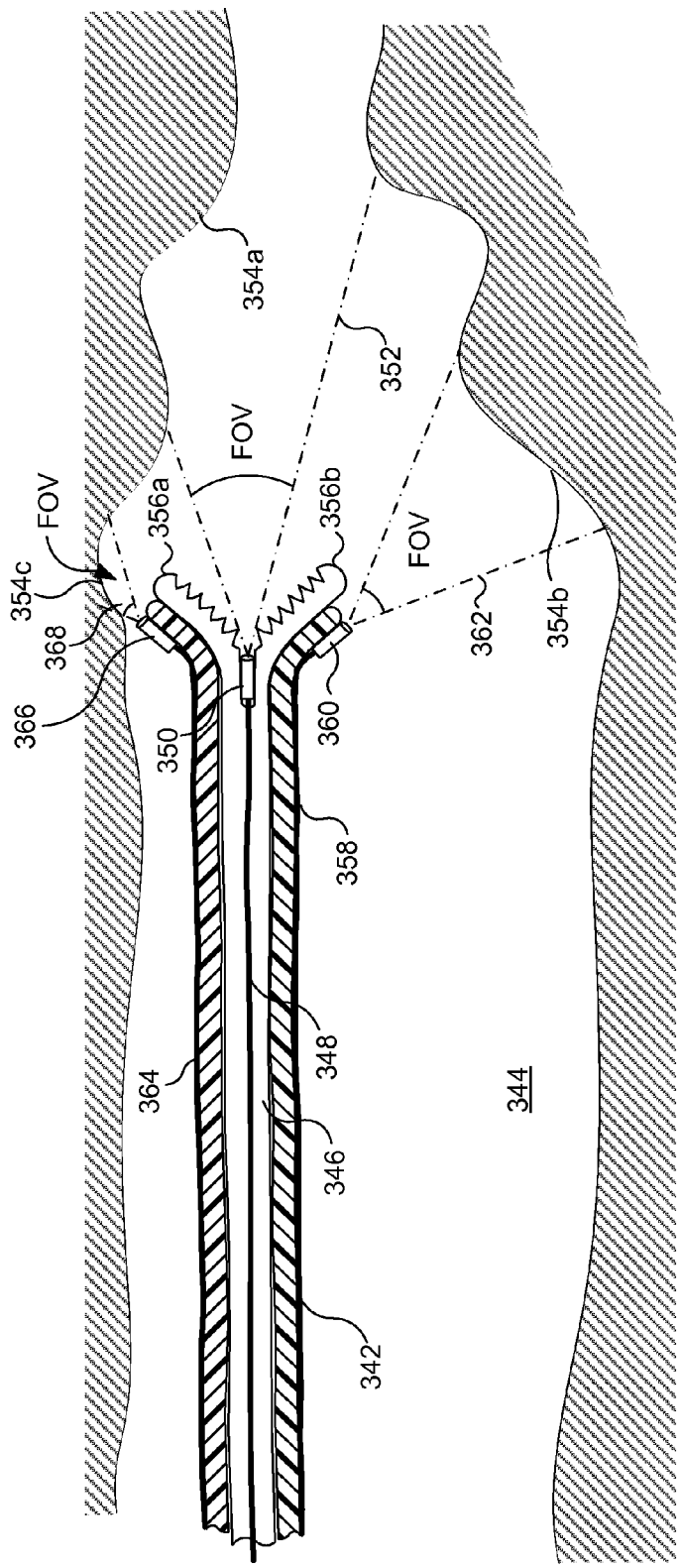
FIG. 13 is a schematic cross-sectional side view of a conduit provided with distal imaging and used to convey a forceps tool having distal imaging, to image multiple views of an internal site.

Providing multiple sites for imaging on a tool and multiple tools with imaging capability for use at a site has clear advantages over a single site for imaging on a tool. An exemplary configuration 340 is illustrated in FIG. 13. In this example, a catheter or conduit 342 is hollow and a forceps tool 346 is passed through the internal lumen formed within the catheter or conduit. A flexible cable 348 extends centrally through an interior of the forceps tool and conveys light and other signals between a proximal end of the forceps tool (not shown) and a scan illuminator 350 that is disposed at the distal end of the forceps tool, between grippers 356a and 356b. Also disposed centrally between the grippers is the distal end of a return optical fiber (not separately shown) that receives light from the site illuminated within an FOV 352 of scan illuminator 350. The light emitted by scan illuminator 350 is directed toward tissue 354a, along a portion of a body lumen 344 in which the configuration has been inserted. The FOV of scan illuminator 350 is forwardly directed relative to the forceps tool and limits the portions of the walls of body lumen 344 that can be seen in the resulting image.

However, catheter or conduit 342 also includes scan illuminators 360 and 366. Flexible cables 358 and 364 extend along opposite sides of the outer surface of the catheter or conduit. A distal end of flexible cable 358 is coupled to scan illuminator 360, while a distal end of flexible cable 364 is coupled to scan illuminator 366. Included within these flexible cables are optical fibers for conveying light and other signals bi-directionally between the scan illuminators and the proximal ends of the flexible cables. Using the light from a proximal source (not shown), the scan illuminator emits light in a desired scan pattern that has a FOV 362 directed to a side of body lumen 344, illuminating tissue 354b that is disposed there. Similarly, scan illuminator 366 emits light in a desired scan pattern that has a FOV 368 directed to illuminate tissue 354c disposed on an opposite side wall of the body lumen. The light received from tissue 354b and 354c is conveyed through return optical fibers within flexible cables 358 and 364, respectively, and is used for producing images of the these different locations that enable a user to more effectively maneuver forceps tool 346 to take a sample of tissue from a desired ROI. Use of multiple images of the interior surface of the body lumen clearly provides much more visual information than using only a single image of a single portion of the body lumen.

Figure 14A:
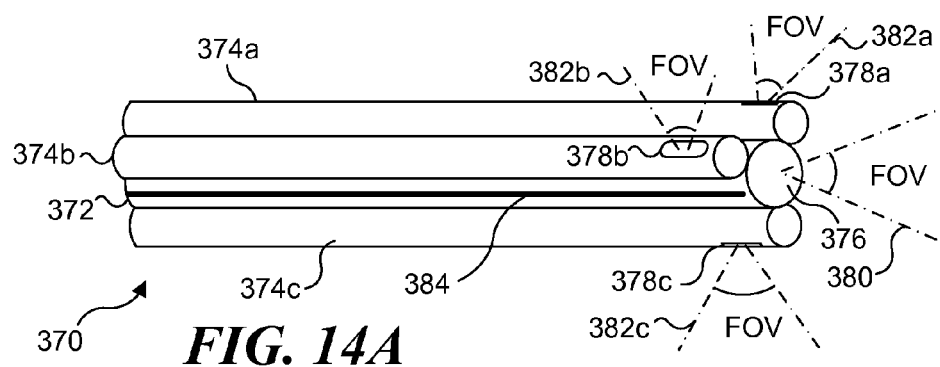
FIG. 14A illustrates a central forward-viewing scanning fiber endoscope (SFE) having a plurality of side-viewing SFEs and a track for conveying a tool to a distal end of the configuration.
Figure 14B:
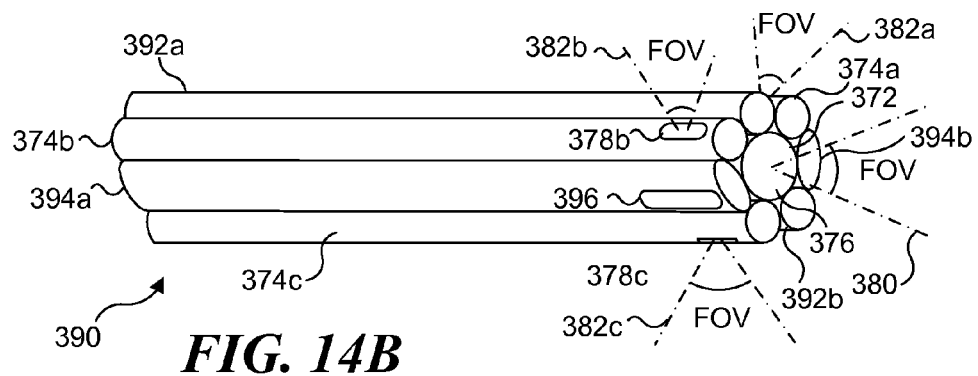
FIG. 14B illustrates a central forward-viewing scanning fiber endoscope (SFE) having a plurality of side-viewing SFEs as well as a plurality of conduits with optional side ports for conveying one or more tools with imaging capability to an internal site.

Two other exemplary configurations 370 and 390 are respectively illustrated in FIGS. 14A and 14B, showing other examples of how imaging can be implemented on multiple tools or other components. In FIG. 14A, exemplary configuration 370 includes a central scanning fiber endoscope (SFE) 372 having forward imaging capability at its distal end 376, and a plurality of SFEs 374a, 374b, and 374c with side imaging capability arrayed around the central SFE. SFEs 374a, 374b, and 374c respectively include side ports 378a, 378b, and 378c through which light is emitted in a desired scanning pattern, so that they provide respective FOVs 382a, 382b, and 382c that are directed in different directions radially around the central SFE. These side-viewing SFEs also each include return optical fibers (not shown) that convey light received from the portion of the site illuminated within their respective FOVs. Central SFE 372 scans light in a desired scanning pattern over a forward FOV 380 and includes a return optical fiber (not shown) that receives light from the portion of a site illuminated by the light in FOV 380. Thus, the combined imaging capability of the four SFEs provides extremely good coverage distally and around the distal end of the configuration. In addition, a guide wire or track 384 extends down at least one side of central SFE 372 and can be employed for advancing any of a number of additional tools or other components toward the distal end of configuration 370. The additional tool or other component may have imaging capability and may include a scan illuminator, or may include only a scan illuminator or a return optical fiber, or may have neither.

In FIG. 14B, exemplary configuration 390 is similar to that of configuration 370, except that it includes conduits 392a and 392b, which do not have imaging capability in this exemplary embodiment and are provided, for example, to convey a fluid to a site or to withdraw fluid from a site, or for carrying out other functions. Moreover, exemplary configuration 390 also includes oval conduit 394a and 394b, which are disposed around central SFE 372, at opposite sides. These oval conduits can optionally each include a side port (such as side port 396, which is shown on oval conduit 394a). The side port can enable another tool or component that is advanced through an interior of the oval conduit to be directed outwardly toward a site, to carry out a desired task such as removing a tissue sample from the site. The compact, generally cylindrical shape of exemplary configurations 370 and 390 provide good protection from surrounding objects (or tissue), but the shape also limits the size of tools that can be advanced along guidewire 384 or through the oval conduits.

Exemplary Multi-Scanner Stereoscope Conduit

Figure 15:
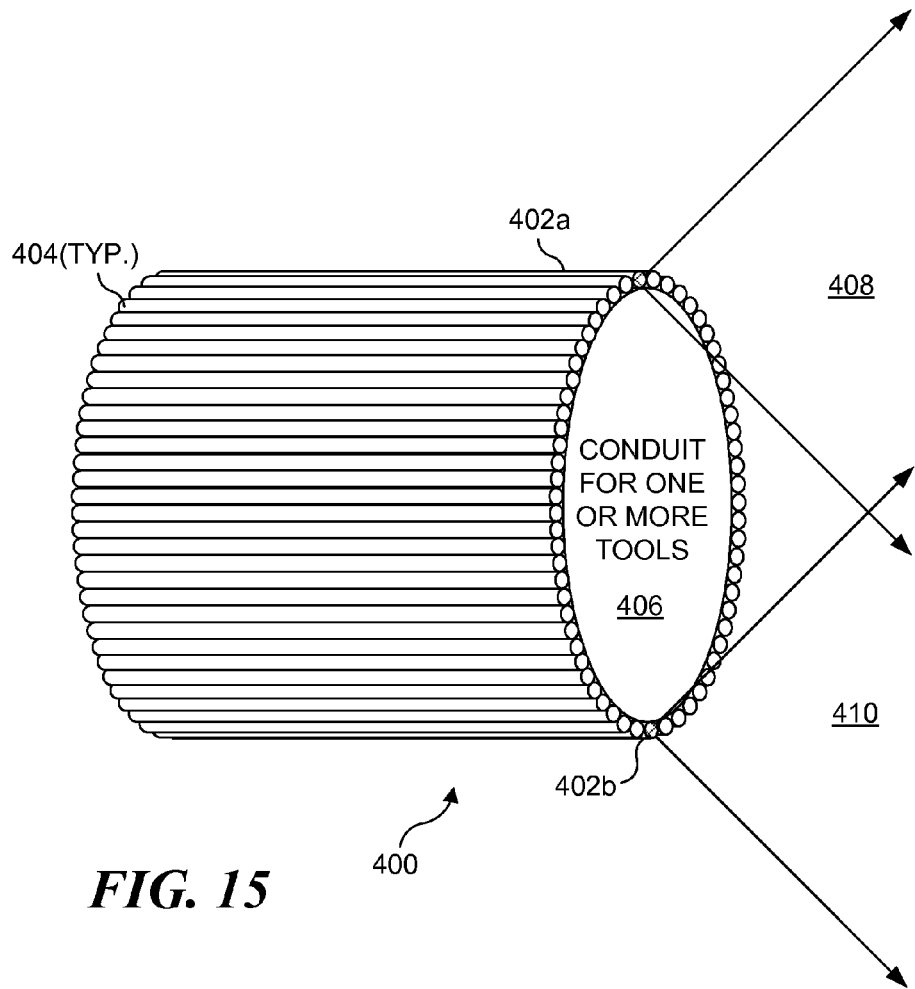
FIG. 15 is a schematic illustration of a distal end of a conduit that can convey one or more tools to a site, which has a plurality of scanning devices mounted around its circumference so that any two or more opposite pairs of scanning devices can be employed for stereographic viewing to provide an image with depth information of a site at which one or more tools are being used.

A tool or conduit that includes at least two disparate scanning devices can be employed to provide a stereoscopic view of a site, which can yield useful depth information that greatly facilitates a user's understanding of the site and makes it possible to more effectively employ tools at the site as a result of that depth information. FIG. 15 illustrates an exemplary embodiment of a conduit 400 having a central lumen 406 through which one or more tools can be advanced to a site at which the one or more tools will be used. In the example shown, a plurality of imaging devices 404 are arranged around the circumference of conduit 400. Any two imaging devices, which will typically be disposed at opposite sides of conduit 400 (not necessarily) can be selectively activated to produce a stereo image of the site. In the example shown in FIG. 15, imaging devices 402a and 402b are activated to scan a site (not shown in this Figure) with two spaced-apart fields of view 408 and 410. The images produced by receiving the light from the site that has been illuminated in the two disparate fields of view can be employed to provide a stereoscopic view of the site, just as the binary vision provided by two spaced-apart eyes does. Different imaging devices 404 can be employed to change the orientation of the stereoscopic image relative to conduit 400, corresponding to the vergence angle of the viewer, or to compensate for rotation of the conduit with respect to the tissue, or to avoid obstruction of the view from specific tools being extended. Imaging devices 402a, 402b, and the other imaging devices 404 can be confocal imaging devices (like those described below in connection with FIGS. 16A, 16B, and 17), or instead can employ imaging devices 404 comprising adjacent light receiver optical fibers, which receive the light from the site illuminated by the disparate fields of view 408 and 410. Light received is conveyed proximally through optical fibers to light sensor (not shown), which produces corresponding electrical signals that can be employed to produce the images used to form the stereoscopic image of the site.

Figure 16A:
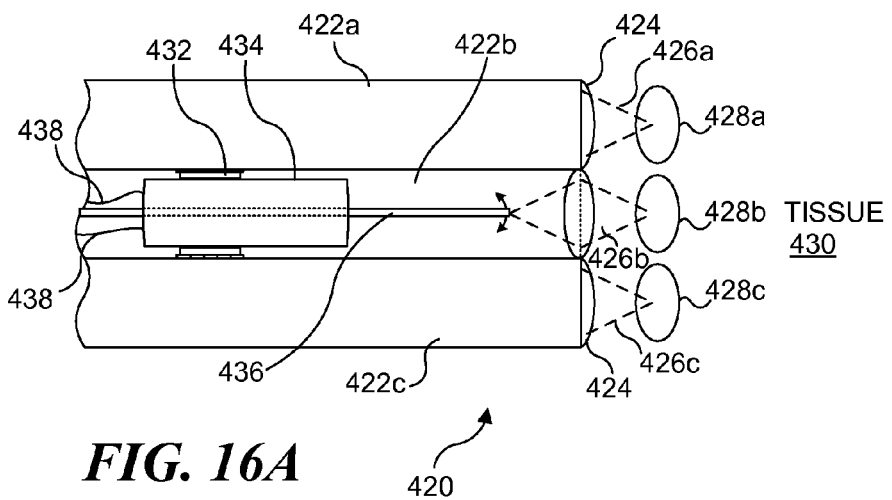
FIG. 16A is a schematic elevational view of a distal portion of an exemplary embodiment of an array of confocal imaging devices, showing details of one of the confocal imaging devices.
Figure 16B:
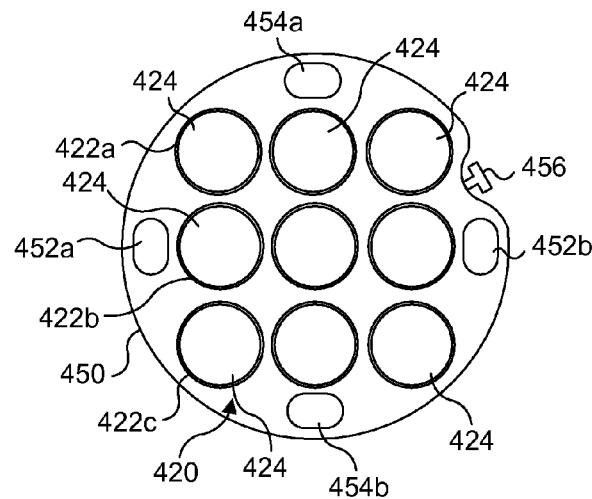
FIG. 16B is a schematic elevational view of a distal surface or end of a tool that includes the array of confocal imaging devices of FIG. 16A.

FIGS. 16A and 16B illustrate an exemplary embodiment showing an array 420 of nine confocal imaging devices; however, it must be emphasized that either more or fewer confocal imaging devices can be used in a tool or other component. Typically, confocal imaging devices have a relatively small FOV, which would limit their usefulness if only a single such device were used to image a site where one or more tools or other components were to be used. However, by combining the images produced by a plurality of such confocal imaging devices to produce an overall image that covers a much larger FOV than any one of the confocal imaging devices, the user can view the image to facilitate the use of the one or more tools or other components at a site.

FIG. 16A illustrates only three confocal imaging devices 422a, 422b, and 422c of the array and shows details of confocal imaging device 422b. In this exemplary embodiment, each confocal imaging device includes at least one lens 424 at its distal end, used to focus light emitted by the confocal imaging devices when scanning a site, such as tissue 430, and to focus light received from the site and conveyed proximally through an optical fiber 436. Light from a source (not shown) is conveyed from the proximal end of optical fiber 436, which passes through a scanning driver 434, so that the distal end of optical fiber 436 is cantilevered from the scanning driver. Scanning driver 434 can be a piezoelectric device having the capability of driving the cantilevered portion of optical fiber 436 to vibrate at or near its resonant frequency in two orthogonal directions when energized by driving signals supplied through leads 438. The scanning driver is itself cantilevered from a cylindrical mount 432 within the confocal imaging device. Confocal imaging devices 422a, 422b, and 422c respectively scan regions 428a, 428b, and 428c with focused scanning spots of light 426a, 426b, and 426c on tissue 430 (or other types of surfaces on a site being imaged). The light returned from the scanning focused spots of light is generally free of crosstalk with the light from others of the confocal imaging devices, because it is produced by light focused on different regions of the site and the light from that specific confocal imaging device is focused back into the core of the cantilevered optical fiber, substantially free of light from the other confocal imaging devices. The scanning of regions 428a, 428b, and 428c is carried out using a desired scanning pattern, such as a helical scan, raster scan, Lissajous scan, or other suitable area scanning pattern, produced by applying appropriate drive signals to the scanning driver through leads 438. Each of the images corresponding to the regions scanned by each confocal imaging device can be combined into an overall image of the site, to facilitate use of tools or other components at the site.

FIG. 16B illustrates the distal surface or end of a tool 450 that includes array 420, showing the nine lenses 424 used by each of the confocal imaging devices comprising the array in this exemplary embodiment. Optionally, stereo non-confocal imaging devices 452a and 452b can be provided at each side of array 420, as well as stereo non-confocal imaging devices 454a and 454b, which are disposed at the upper and lower portions of the distal end of the tool. Alternatively tip bending anchors can instead be anchored at the locations of one or both pairs of the stereo non-confocal imaging devices to bend or deflect the distal end of the tool in a desired direction. If only one pair of tip bending anchors is provided, the tool must be rotated about its longitudinal axis to bend in a different plane. Tool 450 includes at least one track 456 that is disposed on its outer surface and is configured to guide another tool or component to a site to which tool 450 has been advanced. Track 456 is generally T-shaped and extends longitudinally along tool 450 from about the proximal end of the tool to about its distal end.

Figure 17:
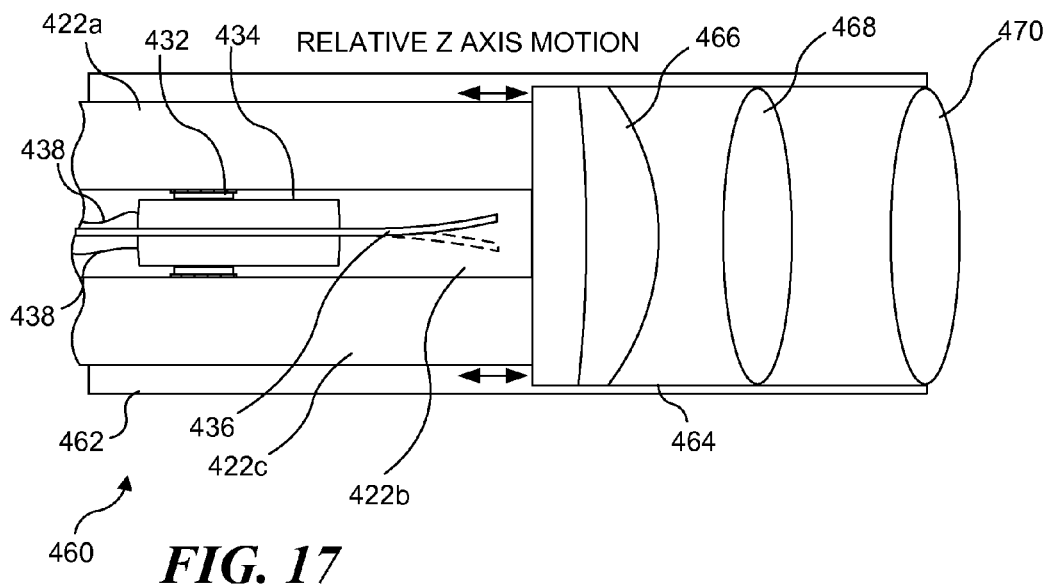
FIG. 17 is a cut-away view of a distal end of an alternative exemplary embodiment of an array of imaging devices that uses a common lens assembly for focusing light onto a site and receiving light from the site for all of the confocal imaging devices in the array.

Yet another exemplary embodiment of a confocal array that is similar to array 420, but uses common lenses 466, 468, and 470 to focus light emitted by all of the confocal imaging devices comprising the array toward different spots on the site and to receive and focus light returned from those spots that are being scanned, back into the distal ends of the cores of the respective cantilevered optical fibers comprising each confocal imaging device. FIG. 17 illustrates a tool 460 that uses this approach and shows the cantilevered distal end of optical fiber 436 being deflected in the desired scanning pattern. Tool 460 can include a track (not shown) like that of tool 450, to guide another tool or component to a site to which tool 460 has been advanced. In addition to scanning each confocal imaging device over a region covered by the FOV of the respective confocal imaging device, tool 460 is configured to vary the depth of the confocal scanning by providing a relative motion between a lens barrel 464 in which lenses 466, 468, and 470 are mounted and a more proximal housing 462 in which the array of confocal imaging devices are mounted, so that the relative motion is along the longitudinal z axis of the tool (as indicated by the arrows). Thus, the depth of confocal scanning with tissue (not shown in this Figure) can be varied as the array of confocal imaging devices scan their respective regions on the site, to provide three-dimensional scanning of the tissue (or other material comprising the site). The lenses or fused lens assembly, such as gradient-index lenses, focus the light for all of the confocal imaging devices of the array, along generally parallel channels, while the focal plane of the array is adjusted along the z axis, using a linear driver (not shown). Alternatively, if a relative motion of the lens assembly is NOT provided, much the same result can be achieved by one of several different methods. Specifically, while not shown, the scanning optical fibers in the various confocal imaging devices can be offset in z distance from the lenses, and/or their orientation can be adjusted, and/or different wavelengths of light can be used to image by each so that the light beams from different confocal imaging devices are focused at different z axis positions. In any of these alternative approaches, more than one depth plane image can be acquired while operating the array of confocal imaging devices at the same time.

Overlap in Confocal Images Produced by An Array of Confocal Imaging Devices

Figure 18A:
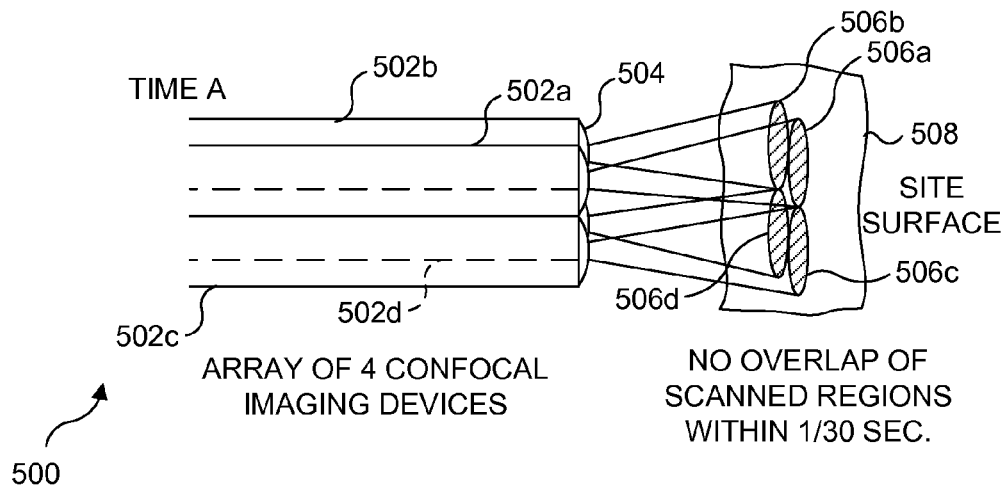
FIG. 18A is a schematic view of the distal end of an exemplary 2×2 array of confocal imaging devices at a time A, showing that there is no overlap at that point in the scanned areas of the four confocal imaging devices on the surface of a site.
Figure 18B:
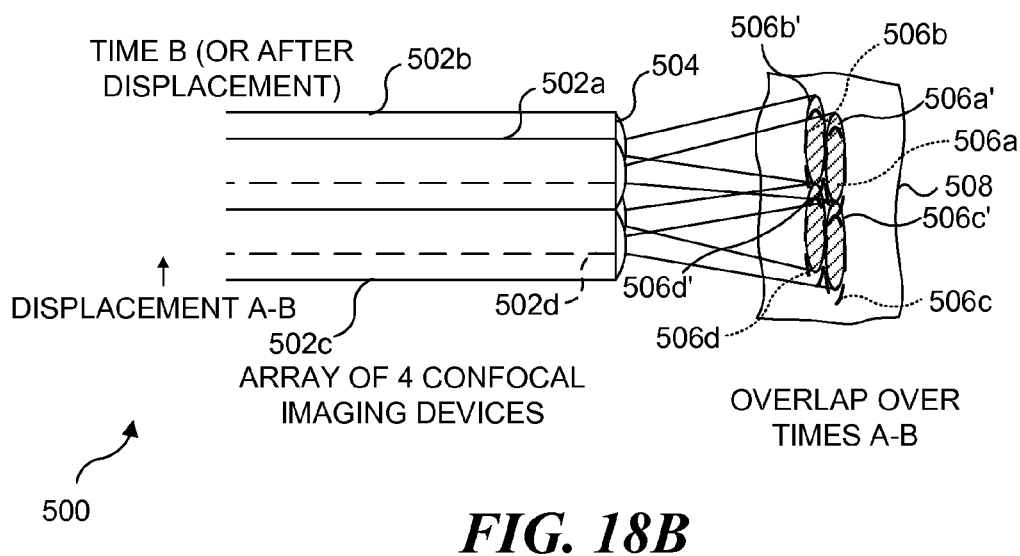
FIG. 18B is a schematic view of the distal end of the 2×2 array of the confocal imaging devices of FIG. 18A, at a later time B (or after a displacement of the array has occurred), showing that the vertical displacement has caused an overlap of the scanned areas, which can produce images that can more readily be stitched together to form an overall image of the site.

FIG. 18A illustrates an exemplary array 500 comprising four confocal imaging device 502a, 502b, 502c, and 502d, which are generally like the confocal imaging devices discussed above. These four confocal imaging devices emit light that is focused by lenses 504 and respectively scan regions 506a, 506b, 506c, and 506d on a site 508. As shown in FIG. 18A, at a time A, there is no overlap between these four scanned regions on the site. The scanning of these regions can occur at $1/30^{th}$ of a second, which is the time required to fully acquire the four images of the site corresponding to these scanned regions in one exemplary embodiment of the confocal imaging devices. However, due to a relative motion between array 500 and site 508, a vertical displacement of the array occurs at a time B, as shown in the example of FIG. 18B. This displacement can be caused by motion of the array due to a user hand-holding it and scanning to cover a larger area of tissue, or moving inadvertently, or because of movement of the site relative to the array. For example, if the site is located in a patient's body, the site may move relative to the array due to a patient's respiration, muscle contraction or body movement, cardiovascular motion, or other physiological causes. The task of producing an overall image of the site based on combining the four images of the site requires that there be at least some overlap of the original scanned regions 506a-506d at time A with scanned regions 506a'-506d' at time B. This overlap between adjacent images can be accentuated by a user intentionally panning the distal end of array 500 over the site, so that appropriate software (discussed below) can be employed to stitch the resulting overlapping images together to form an overall image of the site.

Exemplary Software for Stitching Overlapping Images Together

In a paper by M. Brown and D. G. Lowe, entitled "Recognizing Panoramas," published in the Proceedings of the Ninth IEEE International Conference on Computer Vision (2003), a technique is disclosed for stitching together a plurality of overlapping images to produce an overall panoramic image. This technique is readily employed in connection with stitching together overlapping images of different portions of a site that are produced by a plurality of imaging devices, as discussed above. AUTOSTITCH™ software for carrying out this task can be downloaded from a website: worldwideweb.cs.ubc.ca/~mbrown/autostitch/autostitch.html (where worldwideweb is replaced with "www"). This software can be applied to almost a plurality of digital images that overlap in at least a portion of adjacent images, producing a full image over up to 360×180 degrees, or as large an area as covered by the input images. This software is referenced as only one example of other commercially available software programs that can be employed for stitching together overlapping images to produce an overall combined image of a site.

Figure 19A:
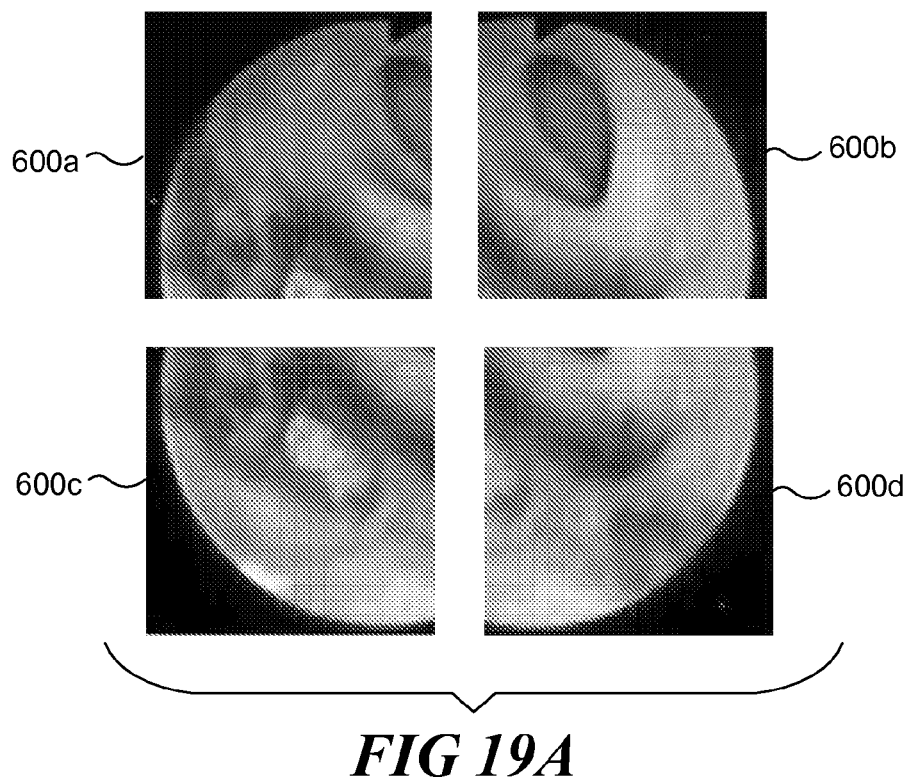
FIG. 19A illustrates four exemplary overlapping images of a pancreatic carcinoma.
Figure 19B:
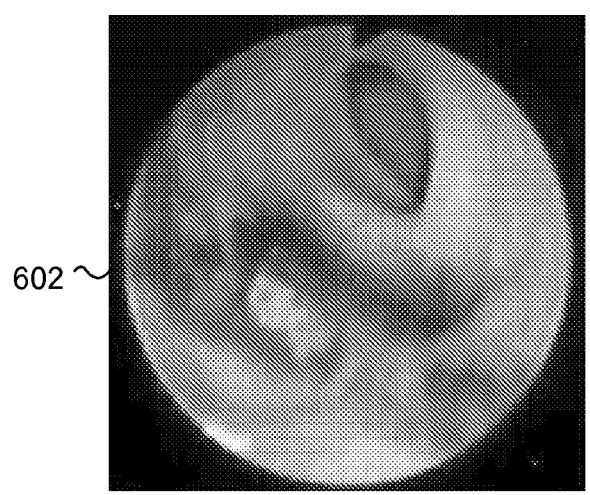
FIG. 19B illustrates an exemplary (simulated) result of stitching together the four images of FIG. 19A to produce an overall image of the site in which the pancreatic carcinoma is readily evident.

FIG. 19A illustrates four exemplary overlapping endoscopic images 600a, 600b, 600c, and 600d of a pancreatic carcinoma (derived from an image in the online "Atlas of Gastroenterological Endoscopy," A. Freytag, T. Deist (2003)) that might represent four overlapping images produced by four scanning devices like those discussed above. These overlapping images can be stitched together using stitching software like that discussed above, to produce an overall image 602 as shown in FIG. 19B. Many other examples of images illustrating the capabilities of such software are provided on the website for the AUTOSTITCH™ software noted above.

Examples Illustrating Adding Imaging Devices to Existing Tool

Figure 20A:
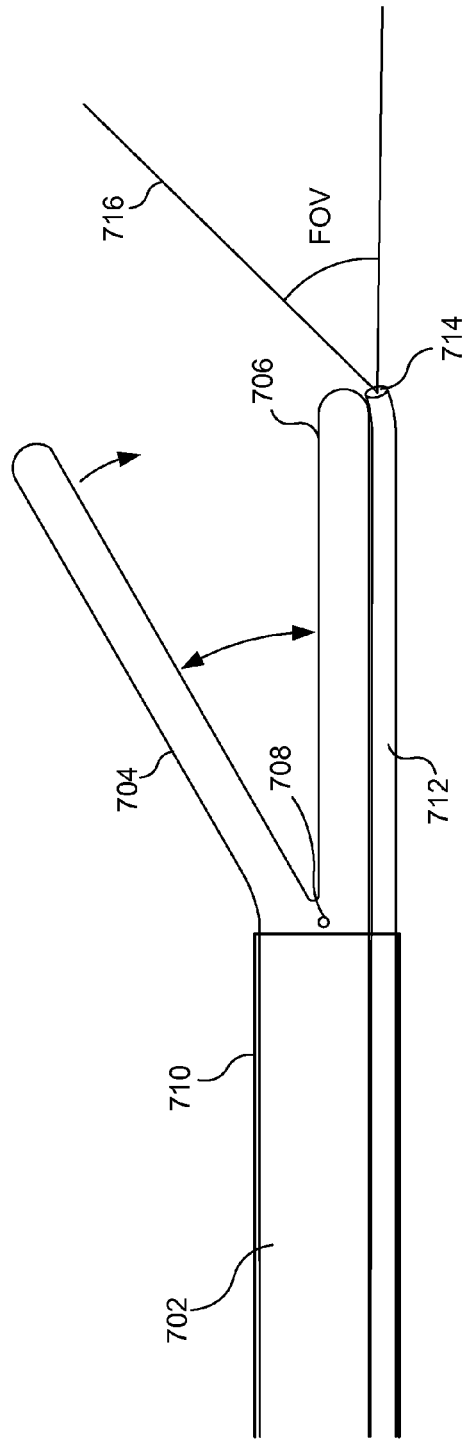
FIG. 20A is a schematic illustration of an existing tool, i.e., a tissue stapler tool, illustrating how an imaging device is coupled to the existing tool with a sheath, to enable imaging of a site where the tool is being used.
Figure 20C:
FIG. 20C is a cross-sectional view of an alternative exemplary embodiment illustrating how two imaging devices can be coupled with a sheath to the existing tool illustrated in FIG. 20A.
Figure 20B:
FIG. 20B is a cross-sectional view of the example of FIG. 20A.

One of the advantages of the compact imaging devices disclosed above is the ease with which they can be coupled to an existing tool or other component to enable imaging of a site that could not be accomplished with larger imaging devices. FIGS. 20A-20C illustrate one exemplary approach 700 that can be employed for adding an imaging device to an existing tool. In this example, the existing tool is a medical stapler 702, or might be an endoscopic linear cutter tool, such as the model i60™ produced by Power Medical Interventions™. As shown in FIG. 20A, the medical stapler includes a movable jaw 704 that pivots around a pivot point 708 toward a fixed jaw 706. To couple an imaging device 712 to the existing medical stapler, a sleeve 710 is slipped over the imaging device and its optical fiber (not separately shown). Sleeve 710 can be formed of a heat shrink tubing so that after being slipped over both the imaging device and medical stapler proximal portion, the sheath can be heated causing it to shrink around both the medical stapler and the imaging device, thereby coupling imaging device 712 to medical stapler 702. A distal end 714 and the portion of imaging device 702 extending beyond sheath 710 can coupled to fixed jaw 706 using a biocompatible adhesive, such as cyanoacrylate, or other suitable adhesive. In this exemplary configuration, distal end 714 is canted upward slightly to direct a FOV 716 of the imaging device distally of the medical stapler (or linear cutter). This arrangement is even more useful if the existing tool is an endoscopic linear cutter, since the FOV will image the site toward which the linear cutter is being advanced to perform its cutting operation.

FIG. 20B illustrates a cross-sectional view of this exemplary embodiment, showing how the sheath has been shrunk to couple imaging device 712 to the existing medical stapler (or endoscopic linear cutter). An alternative exemplary embodiment 720 shown in FIG. 20C illustrates how two imaging devices 712 can similarly be coupled to each side of existing medical stapler (or linear cutting device) 702, using a sheath 722 that has been slipped over both imaging devices and the existing tool and then heated to shrink the sheath tight around the configuration. This exemplary embodiment would be particularly useful if the existing tool is the medical stapler, if the distal ends of the imaging devices are positioned more proximally of the fixed and movable jaws so that the site being stapled is visible in the images produced by the imaging devices, with stereo viewing as an option.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A system that produces a plurality of different images of a site produced by a plurality of imaging devices, while avoiding crosstalk in the images, comprising:
   (a) a plurality of imaging devices, the plurality of imaging devices including a plurality of scanning devices and a plurality of light receivers, each light receiver being associated with one of the plurality of scanning devices to receive light from an area of the site illuminated by said one of the plurality of scanning devices, each scanning device being coupled to a distal end of an optical fiber used to convey light to the scanning device so that the light is emitted by the scanning device to illuminate the site, the light receiver receiving light from the site for use in producing an image of the site;
   (b) at least one light source for supplying light to the scanning devices through a plurality of optical fibers; and
   (c) means for imaging the site so as to prevent crosstalk between the plurality of images, by preventing light emitted by one of the plurality of scanning devices from interfering with light emitted by any other of the plurality of scanning devices, when light that is received from the site by the plurality of light receivers is used to produce a plurality of images of the site.

2. The system of claim 1, further comprising an optical switch that is controlled to direct light from the at least one light source through an optical fiber to a selected one of the plurality of scanning devices at a time.

3. The system of claim 2, wherein the means for imaging so as to prevent crosstalk comprises a controller that is coupled to the optical switch, the controller controlling the optical switch so that only one image of the site is permitted to be captured at a time by the plurality of imaging devices, whereby images of the site are time multiplexed on a frame-by-frame basis.

4. The system of claim 3, wherein the plurality of scanning devices scan the site with light emitted in a desired scanning pattern, followed by a retrace interval to restart another scan, and wherein the controller causes the optical switch to selectively enable light to be supplied to a first scanning device scanning an area of the site while a second scanning device is in the retrace interval, and then causes the optical switch to selectively enable light to be supplied to the second scanning device scanning the area of the site while the first scanning device is in the retrace interval.

5. The system of claim 2, wherein the means for imaging so as to prevent crosstalk comprises a controller that controls the optical switch so that light from the at least one light source is supplied to only one scanning device of a plurality of scanning devices that are scanning an area of the site at a time and only sufficiently long to scan a spot corresponding to a single pixel of an image of the site that is then being captured, whereby images of the site are pixel multiplexed so that the images are captured on a pixel-by-pixel basis, with only one pixel of each of the images being captured at a time.

6. The system of claim 1, wherein the at least one light source comprises a plurality of light sources, and wherein one or more of the plurality of light sources are used only by one of the plurality of scanning devices and produce light at one or more wavebands that are different than the waveband of light produced by any other light source of the plurality of light sources that is used by any other of the plurality of scanning devices to illuminate a common portion of the site.

7. The system of claim 6, wherein the means for imaging so as to prevent crosstalk comprises a plurality of optical filters used to filter the light received by a plurality of light receivers that are receiving light from the common portion of the site illuminated by the plurality of the scanning devices, specific optical filters of the plurality of optical filters passing light in one or more wavebands emitted by the scanning device associated with a specific light receiver, while blocking light in other wavebands emitted by any other scanning device.

8. The system of claim 7, wherein the plurality of optical filters have different polarizations, and wherein the light emitted by each scanning device has a specific polarization corresponding to the polarization of an optical filter used to filter light received by the light receiver associated with the scanning device, so that only the light received from the site that was emitted by the scanning device associated with a specific light receiver is used for producing an image of the site based on the output signal produced in response to the light.

9. The system of claim 1, wherein the means for imaging so as to prevent crosstalk comprises:
   (a) a light modulator that modulates light provided to each scanning device differently; and
   (b) a demodulator that demodulates output signals produced in response to the light received by the plurality of light receivers to separate the output signals based on each different scanning device that produced the light that was reflected from the site and received by the plurality of light receivers, so that only light emitted by the scanning device with which a specific light receiver is associated is used to produce an image.

10. The system of claim 9, wherein the light modulator modulates light using a type of modulation selected from a group consisting of:
   (a) an amplitude modulation; and
   (b) a frequency modulation.

11. A method for avoiding crosstalk in images produced by a plurality of imaging devices used for imaging a site to produce a plurality of images, comprising the steps of:
   (a) conveying light from at least one light source to the plurality of imaging devices, wherein the plurality of imaging devices include a plurality of scanning devices and a plurality of light receivers, each scanning device being coupled to an optical fiber that conveys light from the at least one light source for use in illuminating the site, and each light receiver being associated with a specific scanning device and receiving light from the site;
   (b) emitting the light from each scanning device to illuminate at least a portion of the site;
   (c) responding to the light received from the site by the plurality of light receivers, to produce output signals indicative of the light that was received, for use in producing the plurality of images;
   (d) controlling imaging of the site so as to prevent crosstalk between the plurality of images of the site produced using the light received by the plurality of light receivers, by preventing light emitted by one of the plurality of scanning devices from interfering with light emitted by any other of the plurality of scanning devices, when the light received by each light receiver associated with the one scanning device is used to produce an image of the site.

12. The method of claim 11, wherein the step of controlling the imaging of the site comprises the step of selectively supplying light to only one of the scanning devices at a time, enabling only one image at a time to be captured by the plurality of the imaging devices, so that the images of the site are time multiplexed on a frame-by-frame basis.

13. The method of claim 12, wherein the step of emitting the light from each scanning device comprises the steps of:
   (a) using each scanning device to scan a portion of the site with light emitted in a desired scanning pattern; and
   (b) after completing the scanning by each scanning device in the desired scanning pattern, returning to a start position during a retrace interval to restart another scan with the scanning device.

14. The method of claim 13, wherein the step of imaging includes the step of supplying light to only one imaging device at a time and only sufficiently long to scan a spot corresponding to a single pixel of an image of the site that is being captured, thereby pixel multiplexing images of the site on a pixel-by-pixel basis, by capturing only one pixel of one of the images at a time.

15. The method of claim 11, further comprising the step of supplying light from one or more light sources to only one of the plurality of scanning devices, wherein the one or more light sources operates at one or more wavebands, each of which is different than the waveband of any other light source supplying light to any other of the plurality of scanning devices.

16. The method of claim 15, wherein the step of controlling imaging so as to avoid crosstalk comprises the step of filtering light reaching the light receivers so that only light produced by a scanning device associated with a specific light receiver is used by the specific light receiver for producing one of the plurality of images of the site.

17. The method of claim 11, wherein the step of controlling imaging so as to avoid crosstalk comprises the steps of:
   (a) modulating light provided to each scanning device at different modulation frequencies; and
   (b) demodulating output signals produced in response to light received by the plurality of light receivers, to separate the output signals based on each different scanning device that emitted the light reflected from the site and received by the plurality of light receivers, so that only light from a desired scanning device that was received by a light receiver associated with the desired scanning device is used to produce one of the plurality of images.

18. The method of claim 17, wherein the step of modulating comprises the step of modulating the light with a type of modulation selected from the group consisting of:
   (a) an amplitude modulation; and
   (b) a frequency modulation.

* * * * *